United States Patent
Cloyd

(10) Patent No.: US 11,071,787 B2
(45) Date of Patent: Jul. 27, 2021

(54) TOPIRAMATE COMPOSITIONS AND METHODS OF MAKING AND USING THE SAME

(71) Applicant: REGENTS OF THE UNIVERSITY OF MINNESOTA, St. Paul, MN (US)

(72) Inventor: James C. Cloyd, Edina, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 166 days.

(21) Appl. No.: 15/254,195

(22) Filed: Sep. 1, 2016

(65) Prior Publication Data
US 2017/0043019 A1 Feb. 16, 2017

Related U.S. Application Data

(60) Division of application No. 12/407,734, filed on Mar. 19, 2009, now abandoned, which is a continuation-in-part of application No. 11/855,642, filed on Sep. 14, 2007, now abandoned.

(60) Provisional application No. 60/844,875, filed on Sep. 15, 2006.

(51) Int. Cl.
| | |
|---|---|
| *A61K 31/724* | (2006.01) |
| *A61K 47/40* | (2006.01) |
| *A61K 31/357* | (2006.01) |
| *A61K 9/00* | (2006.01) |

(52) U.S. Cl.
CPC ............ *A61K 47/40* (2013.01); *A61K 9/0019* (2013.01); *A61K 31/357* (2013.01); *A61K 31/724* (2013.01)

(58) Field of Classification Search
CPC ..... A61K 47/40; A61K 31/357; A61K 9/0019
USPC .......................................................... 514/58
See application file for complete search history.

(56) References Cited

U.S. PATENT DOCUMENTS

| | | | |
|---|---|---|---|
| 5,362,860 A | 11/1994 | Huang | |
| 2003/0235576 A1* | 12/2003 | Duettmann | A61K 31/473 424/94.64 |
| 2006/0182684 A1* | 8/2006 | Beliveau | C07K 14/47 424/1.69 |
| 2008/0206146 A1 | 8/2008 | Akhtari | |
| 2014/0018362 A1 | 1/2014 | Gustein | |

FOREIGN PATENT DOCUMENTS

| | | |
|---|---|---|
| CN | 101966196 A | 2/2011 |
| WO | WO-9111172 A1 * | 8/1991 |
| WO | WO 2010/045281 | 4/2010 |
| WO | WO 2011-149349 A1 | 12/2011 |

OTHER PUBLICATIONS

Kellett et al. (J Neurol Neurosurg Psychiatry 1999;66:759-763).*
Ortho-McNeil Neurologies, Inc., Topamax, Product package insert, (2005).*
Follett et al. (The Journal of Neuroscience, May 5, 2004, 24(18): 4412-4420).*
Monnaert et al. (The Journal of Pharmacology and Experimental Therapeutics, 2004, vol. 310, No. 2, p. 745-751).*
Clark, et al., Intravenous topiramate: Comparison of pharmacokinetics and safety with the oral formulation in healthy volunteers, Epilepsia. Jun. 2013;54(6):1099-1105.
Clark, et al., Intravenous topiramate: Comparison of pharmacokinetics and safety with the oral formulation in healthy volunteers, Epilepsia, Jan. 7, 2013, doi: 10.1111/epi 12134.
Clark, et al., Intravenous topiramate: Safety and pharmacokinetics following a single dose in patients with epilepsy or migraines taking oral topiramate, Epilepsia. Jun. 2013; 54(6):1106-1111.
Monnaert, V., et al., Behavior of α-, β-, and γ-Cyclodextrins and Their Derivatives on an in Vitro Model of Blood-Brain Barrier, *J. Pharmacol Exp Ther*, 310(2):745-751, 2004.
Monnaert, V., et al., Effects of γ- and Hydroxypropyl-γ-cyclodextrins on the Transport of Doxorubicin across an in Vitro Model of Blook-Brain Barrier, *J. Pharmacol Exp Ther*, 311(3):1115-1120, 2004.
Pardridge, William M., The Blood-Brian Barrier: Bottleneck in Brain Drug Development, *NeuroRx: The Journal of the American Society for Experimental Neuro Therapeutics*, 2(1):3-14, 2005.
Rasheed, Arun, et al., Cyclodextrins as Drug Carrier Molecule: A Review, *Sci Pharm*, 76:567-598, 2008.
Arima, H, et al. "Comparative Studies of the Enhancing Effects of Cyclodextrins on the Solubility and Oral Bioavailability of Tacrolimus in Rats" J Pharm Studies 90:690-701 (2001).
Cutrignelli, et al., Comparative effects of some hydrophilic excipients on the rate of gabapentin and baclofen lactamization in lyophilized formulations, International Journal of Pharmaceutics 332:98-106 (2007).
Loftsson, T., et al, "Cyclodextrin-accelerated degradation of β-lactam antibiotics in aqueous solutions" Int J of Pharm 67:R5-R7 (1991).
Szejtli, J., :Cyclodextrins and their Inclusion Complexes Akademiai Kiado, Budapest (1982).
Szejtli, J., "Cyclodextrins in Drug Formulations: Part II" Pharm Tech 15(8):24-38 (1991).
Ueda, et al, Evaluation of Sulfobutyl Ether B-Cyclodextrin as a Solubilizing/Stabilization Agent for Several Drugs, Drug Development and Industrial Pharmacy, 24(9):863-867 (1998).

* cited by examiner

*Primary Examiner* — Shaojia A Jiang
*Assistant Examiner* — Michael C Henry
(74) *Attorney, Agent, or Firm* — Knobbe, Martens, Olson & Bear LLP

(57) ABSTRACT

The present invention is directed to compositions comprising topiramate and a sulfoalkyl ether cyclodextrin, and methods of making and using the same.

20 Claims, 9 Drawing Sheets

TOPIRAMATE COMPOSITIONS AND METHODS OF MAKING AND USING THE SAME

CROSS-REFERENCE TO RELATED APPLICATIONS

This application is a division of U.S. Ser. No. 12/407,734 filed Mar. 19, 2009 which is a Continuation-In-Part of U.S. application Ser. No. 11/855,642, filed Sep. 14, 2007, now abandoned, which claims the benefit of the filing date of U.S. Appl. No. 60/844,875, filed Sep. 15, 2006, each of which is herein incorporated by reference in its entirety.

STATEMENT OF GOVERNMENT RIGHTS

This invention was made with government support under NS016308 awarded by the National Institutes of Health. The government has certain rights in the invention.

BACKGROUND OF THE INVENTION

Field of the Invention

The present invention is related to compositions comprising topiramate and a sulfoalkyl ether cyclodextrin, methods of making the compositions, and methods of treating subjects in need thereof.

Background Art

Topiramate (2,3:4,5-di-O-isopropylidene-β-D-fructopyranose sulfamate, $C_{12}H_{21}NO_8S$, molecular weight 339.36) is a sulfamate-substituted monosaccharide, related to fructose, and is an anticonvulsant. Topiramate is approved as initial monotherapy in epilepsy patients 10 years of age and older with partial onset or primary generalized tonic-clonic seizures. Topiramate is also approved as adjunctive therapy in epilepsy adult and pediatric epilepsy patients 2-16 years of age with partial onset seizures, or primary generalized tonic-clonic seizures, and in patients 2 years of age and older with seizures associated with Lennox-Gastaut syndrome (a disorder that causes seizures and developmental delay). Topiramate is also approved in adults for the prophylaxis of migraine headache. Topiramate has also found off-label use as an antidepressant, and treatment for bipolar disorder, alcoholism, bulimia nervosa, obsessive-compulsive disorder, smoking cessation, and neuropathic pain.

More recently, topiramate has been studied for treatment of seizures and neuroprotection in neonates suffering from hypoxic-ischemic encephalopathy. See, e.g., U.S. Pat. No. 6,921,775, the entire content of which is hereby incorporated by reference. Specifically, periventricular leukomalacia is a form of hypoxic-ischemic cerebral white matter injury seen most commonly in premature infants and is the major antecedent of cerebral palsy. Glutamate receptor-mediated excitotoxicity is a predominant mechanism of hypoxic-ischemic injury to developing cerebral white matter. It has been demonstrated that AMPA receptors are expressed on developing human oligodendrocytes that populate fetal white matter at 23-32 weeks gestation, the period of highest risk for periventricular leukomalacia, and that administration of topiramate post-insult in vivo, is protective against selective hypoxic-ischemic white matter injury and decreases the subsequent neuromotor deficits. Topiramate attenuates AMPA-kainate receptor-mediated cell death and calcium influx, as well as kainate-evoked currents in developing oligodendrocytes, similar to the AMPA-kainate receptor antagonist 6-nitro-7-sulfamoylbenzo-(f)quinoxaline-2,3-dione (NBQX).

Topiramate is currently available as oral dosage forms (TOPAMAX® oral tablets, in 25 mg, 50 mg, 100 mg and 200 mg dosages, and TOPAMAX SPRINKLE® oral capsules, in 15 mg and 25 mg dosages).

In addition, orally administered topiramate is quickly absorbed, and about 70% of an oral topiramate dose is excreted in the urine as unchanged drug. The remainder is extensively metabolized by hydroxylation, hydrolysis, and glucuronidation. It has been previously found that the bioavailability of an oral topiramate dose is about 80%. However, an oral dose can be susceptible to factors that limit its bioavailability such as first-pass hepatic metabolism and/or limited absorption in the gastro-intestinal tract. Thus, the bioavailability of an oral dose can differ significantly from the bioavailability of an injectable dose. In addition, pediatric patients have a 50% higher clearance and consequently shorter elimination half-life for topiramate compared to adults. Consequently, the plasma concentration for the same mg/kg dose may be lower in pediatric patients compared to adults. Thus, identification of an injectable topiramate dosage regimen for both adults, pediatric subjects and neonates is also needed, which requires determination of the bioavailability and pharmacokinetic behavior of injectable topiramate in these subject populations.

BRIEF SUMMARY OF THE INVENTION

As described herein, compositions suitable for injectable administration that include topiramate and a cyclodextrin have been developed. These injectable compositions are useful, e.g., for treating patient populations for which oral compositions of topiramate are not appropriate. For example, oral compositions of topiramate may not be appropriate because a patient may be too young, unable to swallow, undergoing GI surgery, incapacitated, or have a disorder that blocks absorption. Further, injectable compositions of topiramate would be useful for treating conditions where patients need to rapidly attain an increased concentration of topiramate. These injectable compositions also provide a more controlled dosing than do oral compositions.

The present invention is directed to a composition comprising topiramate, or a salt thereof, and compound of Formula I:

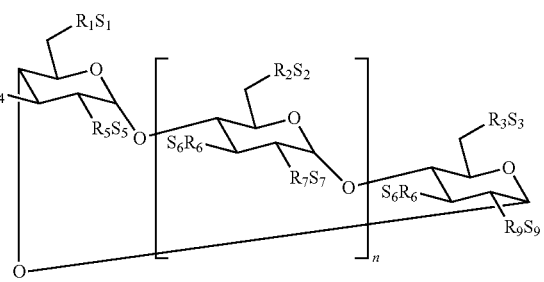

wherein: n is 4, 5 or 6; $R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$ and $S_9$ are each, independently, H or a pharmaceutically acceptable cation.

In some embodiments, at least one of $R_1$ and $R_2$ is independently a —O—($C_2$-$C_6$ alkylene)-$SO_3^-$ group that is a —O—$(CH_2)_m SO_3^-$ group, wherein m is 2 to 6, and the pharmaceutically acceptable cation is H, an alkali metal, an alkaline earth metal, an ammonium ion, or an amine cation.

In some embodiments, the compound of Formula I is a compound of Formula III:

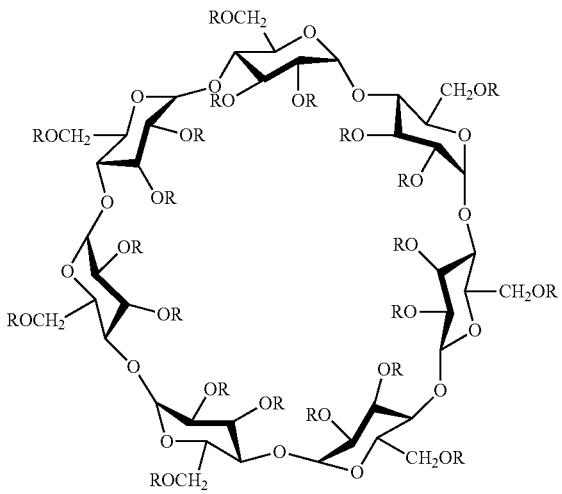

wherein R=$(H)_{21-x}$ or $(—(CH_2)_4—SO_3Na)_x$. In some embodiments, x=6.0-7.1.

In some embodiments, the compound of Formula I is present in the composition at a concentration of about 1 mg/mL to about 700 mg/mL.

In some embodiments, the topiramate is present in the composition at a concentration of about 5 mg/mL to about 100 mg/mL, about 5 mg/mL to about 50 mg/mL, or about 10 mg/mL to about 20 mg/mL.

In some embodiments, the compound of Formula I and topiramate are present in a ratio of about 1.4:1, about 1.4:1 or greater, or about 1.4:1 to about 5:1.

In some embodiments, the composition further comprises a pharmaceutically acceptable carrier.

In some embodiments, the composition of the present invention is stable at 25° C. for a period of at least 12 weeks. In some embodiments, the composition of the present invention is stable at 40° C. for a period of at least 12 weeks.

In some embodiments, the composition of the present invention provides a similar bioavailability of topiramate upon either intravenous administration or oral administration to a subject.

The present invention is also directed to a method for delivering topiramate to a patient, comprising administering the composition of the present invention to the patient.

The present invention is also directed to a method for treating a patient who has or is at risk for developing a condition amenable to treatment with topiramate, the method comprising parenterally administering an effective amount of the composition of the present invention to the patient so as to treat the condition.

In some embodiments, the condition is selected from epilepsy, seizures, status epilepticus, refractory status epilepticus, gambling addiction, migraines, substance dependence, alcoholism, cocaine dependence, nicotine dependence, metabolic syndrome X, diabetes mellitus, type 2, vomiting, obsessive-compulsive disorder, refractory generalized social phobia, Tourette syndrome, levodopa-induced dyskinesia in Parkinson's Disease, refractory POS, Prader-Willi syndrome, multiple sclerosis, Lennox-Gastaut syndrome, Dravet's syndrome, bipolar disorder, obesity, post traumatic stress disorder, cluster headaches, severe headaches, and conditions caused by exposure to a chemical warfare nerve agent.

The present invention is also directed to a method for providing neuroprotection in a patient, comprising administering an effective amount of the composition of the present invention intravenously to the patient. In some embodiments, the neuroprotection is needed during surgery. In some embodiments, the patient in need of neuroprotection is undergoing cardiac surgery or neurosurgery. In some embodiments, the patient in need of neuroprotection is a neonatal patient. In some embodiments, the patient in need of neuroprotection is a neonatal patient suffering from hypoxic-ischemic encephalopathy, subdural hematoma, or infection.

The present invention is also directed to a method of administering the composition of the present invention wherein oral topiramate therapy for the patient has been interrupted.

In some embodiments, the patient is a neonatal patient. In some embodiments, the neonatal patient suffers from hypoxic-ischemic encephalopathy, subdural hematoma, or infection. In some embodiments, the patient is a pediatric patient, an adult patient, or a geriatric patient.

In some embodiments, the composition of the present invention is administered once daily, twice daily, or more frequently.

In some embodiments, the effective amount comprises about 0.2 mg/kg/day to about 50 mg/kg/day topiramate, about 0.5 mg/kg/day to about 15 mg/kg/day topiramate, about 1 mg/kg/day to about 10 mg/kg/day topiramate, or about 1 mg/kg/day to about 5 mg/kg/day topiramate.

The present invention is also directed to a method wherein the composition of the present invention is administered intravenously and has a similar effectiveness as a similar dose of topiramate that is orally administered.

The present invention is also directed to a method for treating anoxia in a patient, the method comprising parenterally administering an effective amount of the composition of the present invention to the patient suffering from anoxia.

The present invention is also directed to a method for treating seizures in a patient, the method comprising parenterally administering an effective amount of the composition of the present invention to the patient suffering from seizures.

The present invention is also directed to a method for treating a stroke in a patient, the method comprising parenterally administering an effective amount of the composition of the present invention to the patient suffering from stroke.

The present invention is also directed to a method for loading a patient to attain an effective topiramate concentration, the method comprising parenterally administering to the patient an amount of the composition of the present invention comprising a topiramate loading dose. In some embodiments, the topiramate loading dose, LD(mg), is an amount of topiramate given by:

$$LD(mg)=[TPM(mg/L)]\times(0.7\ L/kg)\times(P(kg))$$

where [TPM(mg/L)] is a target change in the in vivo topiramate concentration of the patient, and P(kg) is the mass of the patient in kilograms.

BRIEF DESCRIPTION OF THE FIGURES

The following drawings are given by way of illustration only, and thus are not intended to limit the scope of the present invention.

DETAILED DESCRIPTION OF THE INVENTION

Figure 1:
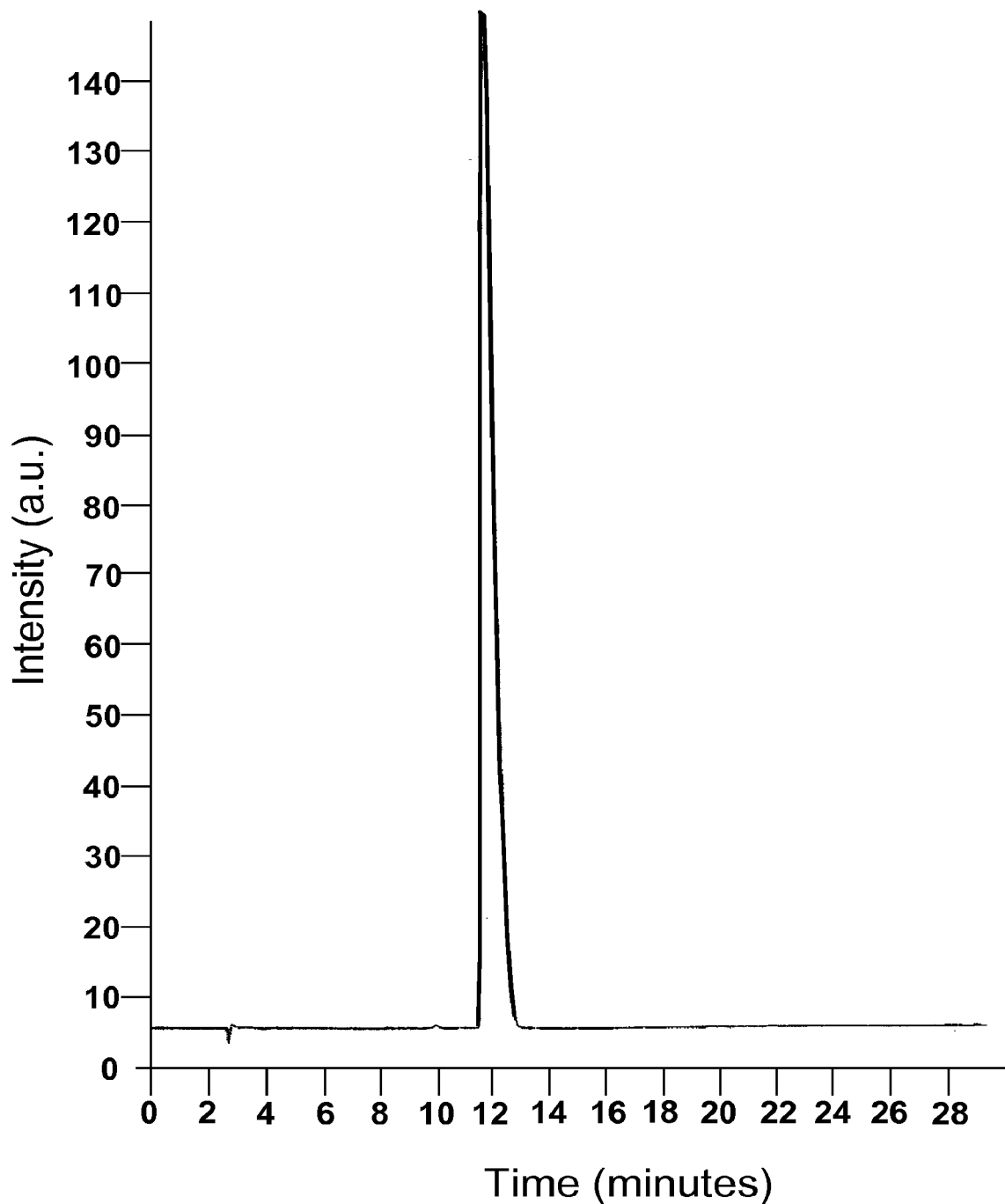
FIG. 1 depicts a chromatogram from injection of a topiramate standard.

In view of the above description and the examples below, one of ordinary skill in the art will be able to practice the invention as claimed without undue experimentation. The foregoing will be better understood with reference to the following examples that detail certain procedures for the preparation of compositions and formulations according to the present invention. All references made to these examples are for the purposes of illustration. The following examples should not be considered exhaustive, but merely illustrative of only a few of the many embodiments contemplated by the present invention.

Accordingly, certain embodiments of the present invention provide compositions comprising topiramate, or a salt thereof, and compound of Formula I:

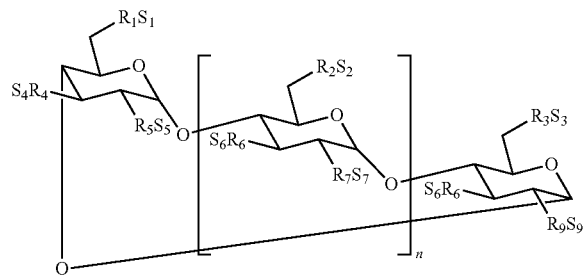

I wherein: n is 4, 5 or 6; $R_1$, $R_2$, $R_3$, $R_4$, $R_5$, $R_6$, $R_7$, $R_8$ and $R_9$ are each, independently, —O— are a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$ and $S_9$ are each, independently, H or a pharmaceutically acceptable cation.

Certain embodiments of the present invention provide compositions prepared by combining topiramate, or a salt thereof, and a compound of Formula I:

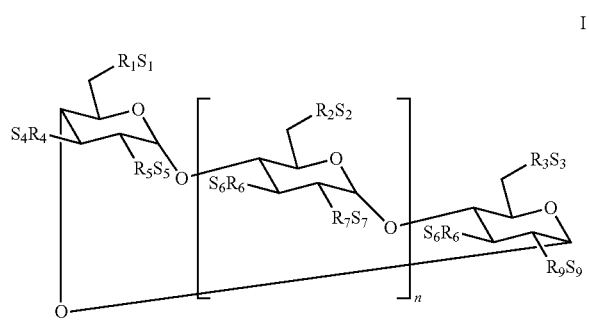

I wherein: n is 4, 5 or 6; $R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$ and $S_9$ are each, independently, H or a pharmaceutically acceptable cation.

In some embodiments of the invention, at least one of $R_1$ and $R_2$ is independently a —O—($C_2$-$C_6$ alkylene)-$SO_3^-$ group that is a —O—$(CH_2)_m SO_3^-$ group, wherein m is 2 to 6.

In some embodiments of the invention, the pharmaceutically acceptable cation is H, an alkali metal, an alkaline earth metal, an ammonium ion, or an amine cation.

Certain embodiments of the present invention provide compositions comprising topiramate, or a salt thereof, and a cyclodextrin such as a compound of Formula III:

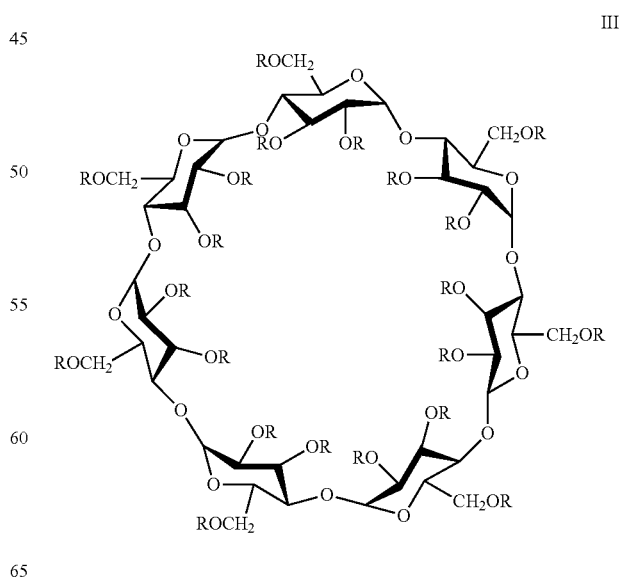

III wherein $R=(H)_{21-x}$ or $(—(CH_2)_4—SO_3Na)_x$. In some embodiments of the invention, x=6.0-7.1.

Certain embodiments of the present invention provide compositions prepared by combining topiramate, or a salt thereof, and a cyclodextrin such as a compound of Formula III:

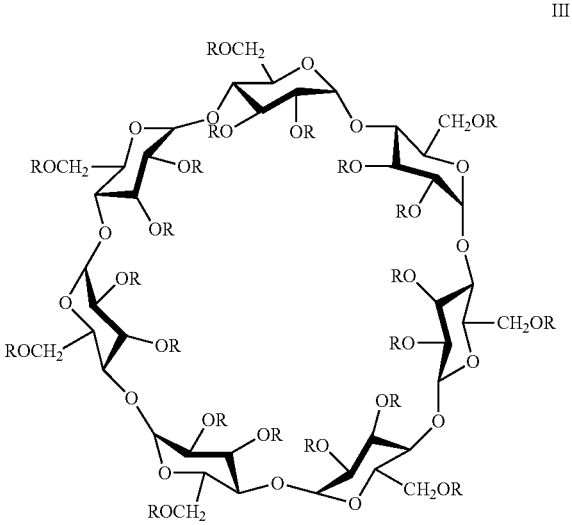

III wherein $R=(H)_{21-x}$ or $(-CH_2)_4-SO_3Na)_x$. In some embodiments of the invention, $x=6.0-7.1$.

In some embodiments of the invention, the composition of the invention further comprises an additional therapeutic agent. Additional therapeutic agents suitable for use with the present invention (as either present in the composition or as administered to a subject in a separate composition) include, but are not limited to, stimulants, anti-epileptic medications, migraine medications (e.g., prophylactic migraine therapeutics and migraine-release therapeutics), and the like, and combinations thereof.

In some embodiments of the invention, the composition further comprises an additional pharmaceutically acceptable carrier.

In some embodiments of the invention, the composition is suitable for injectable administration to a patient. In some embodiments of the invention, the composition is suitable for intravenous or intramuscular administration to a patient.

Certain embodiments of the present invention provide methods for delivering topiramate to a patient, comprising administering a composition of the invention to the patient. In some embodiments of the invention, the patient is a patient in need of treatment with topiramate. In some embodiments of the invention, the composition is administered intravenously to the patient. In some embodiments of the invention, the composition is administered intramuscularly to the patient.

Certain embodiments of the present invention provide methods for treating a patient who has or is at risk for developing a condition amenable to treatment with topiramate comprising administering an effective amount (i.e., a therapeutically effective amount) of a composition of the invention (e.g., intravenously or intramuscularly) to the patient so as to treat the condition.

In some embodiments of the invention, the condition is selected from epilepsy, seizures, status epilepticus, refractory status epilepticus, gambling addiction, migraines, substance dependence, alcoholism, cocaine dependence, nicotine dependence, metabolic syndrome X, diabetes mellitus, type 2, vomiting, obsessive-compulsive disorder, refractory generalized social phobia, Tourette syndrome, levodopa-induced dyskinesia in Parkinson's Disease, refractory POS, Prader-Willi syndrome, multiple sclerosis, Lennox-Gastaut syndrome, Dravet's syndrome, bipolar disorder, obesity, post traumatic stress disorder, cluster headaches, severe headaches, and conditions caused by exposure to a chemical warfare nerve agents such as sarin.

Certain embodiments of the present invention provide methods for providing neuroprotection in a patient, comprising administering a therapeutically effective amount of a composition of the invention (e.g., intravenously) to the patient. In some embodiments, the neuroprotection is needed after a head trauma. In some embodiments of the invention, the neuroprotection is needed before, during and/or after surgery. In some embodiments of the invention, the neuroprotection is needed before, during and/or after cardiac surgery; or before, during and/or after neurosurgery. In some embodiments, a subject in need of neuroprotection is a neonate suffering from hypoxic-ischemic encephalopathy, subdural hematoma, or infection. In some embodiments, the composition of the present invention is administered to the neonate.

The present invention is also directed to a method for treating periventricular leukomalacia ("PVL"), mental retardation, and/or neonatal stroke in a human subject, the method comprising administering to the human subject the composition of the present invention in a therapeutically effective amount such that PVL, mental retardation, and/or neonatal stroke is treated. In some embodiments, the human subject is a neonate.

In some embodiments, the composition of the present invention is administered to a pregnant mother in a therapeutically effective amount to provide neuroprotection to a fetal subject in need thereof. Thus, the present invention is also directed to a method for treating PVL, mental retardation, and/or stroke in a human fetus comprising administering to a pregnant mother topiramate and a pharmaceutically acceptable carrier such that PVL, mental retardation, and/or stroke is treated in the fetus. The present invention is also directed to a method for treating grey and/or white matter injury in the brain of a fetal subject comprising administering to a pregnant mother the composition of the present invention in a therapeutically effective amount such that grey and/or white matter injury in the brain of the fetal subject is treated.

The present invention is also directed to a method for treating grey and/or white matter injury in the brain of a perinatal subject comprising administering to the perinatal subject the composition of the present invention in a therapeutically effective amount such that grey and/or white matter injury in the brain is treated.

Certain embodiments of the present invention provide methods for treating anoxia in a patient, comprising administering an effective amount of a composition of the invention (e.g., intravenously) to the patient.

Certain embodiments of the present invention provide methods for treating seizures in a patient, comprising administering an effective amount of a composition of the invention (e.g., intravenously) to the patient. As used herein, the term "seizures" includes but is not limited to, partial seizures, including without limitation; simple partial seizures, complex partial seizures, and secondarily generalized seizures; generalized seizures, including without limitation absence seizures (also called "petit mal") typical absence seizures, atypical absence seizures, myoclonic seizures, tonic seizures, clonic seizures, generalized tonic-clonic seizures (also called "grand mal"), and atonic seizures; and seizures associated with juvenile myoclonic epilepsy, Lennox-Gastaut syndrome, Dravet's syndrome, and hypoxic-ischemic encephalopathy.

Certain embodiments of the present invention provide methods for loading a patient to attain an effective topiramate concentration, comprising administering an effective amount of a composition of the invention (e.g., intravenously) to the patient. As used herein, a "loading dose" refers to an initial higher dose of topiramate that is administered at the beginning of a course of treatment before a lower maintenance dose is started.

In some embodiments of the invention, oral topiramate therapy for the patient has been interrupted. For example, a composition of the present invention can be parenterally administered to a subject upon re-starting administration of topiramate as either of an adjunctive or a monotherapy in a patient.

In some embodiments of the invention, the patient is a neonatal patient.

Certain embodiments of the present invention provide compositions of the invention for use in medical treatment or diagnosis.

Certain embodiments of the present invention provide use of topiramate, or a salt thereof, and compound of Formula I:

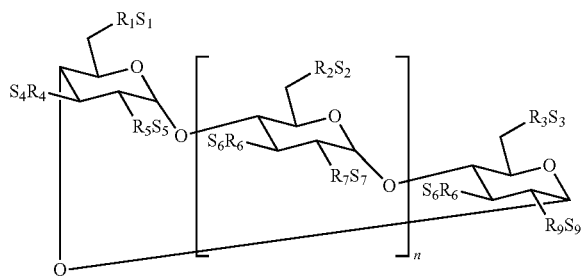

wherein: n is 4, 5 or 6; $R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$ and $S_9$ are each, independently, a pharmaceutically acceptable cation, to prepare a medicament useful for treating a condition amenable to treatment with topiramate in an animal.

Certain embodiments of the present invention provide the use of topiramate, or a salt thereof, and a cyclodextrin such as a compound of Formula III: wherein R═(H)$_{21-x}$ or (—($CH_2$)$_4$—$SO_3$Na)$_x$, to prepare a medicament useful for treating a condition amenable to treatment with topiramate in an animal. In some embodiments of the invention, on average, x=6.0-7.1.

Certain embodiments of the present invention provide the use of a composition of the invention to prepare a medicament useful for treating a condition amenable to treatment with topiramate in an animal.

In some embodiments of the invention, the medicament is suitable for injectable (e.g., intravenous) administration to a patient.

Compositions for injectable (e.g., IV) administration of topiramate and a cyclodextrin have been developed.

In certain embodiments, the composition of the invention comprises topiramate and a sulfoalkyl ether cyclodextrin of the Formula I:

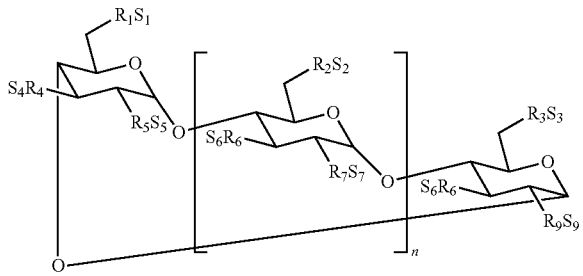

wherein: n is 4, 5 or 6; $R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group, preferably a —O—($CH_2$)$_m$$SO_3^-$ group, wherein m is 2 to 6, preferably 2 to 4, (e.g., —O—$CH_2CH_2CH_2SO_3^-$ or —O—$CH_2CH_2CH_2CH_2SO_3^-$); and $S_1$, $S_2$, $S_3$, $S_4$, $S_5$, $S_6$, $S_7$, $S_8$ and $S_9$ are each, independently, H or a pharmaceutically acceptable cation which includes, for example, alkali metals (e.g., $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine and ($C_4$-$C_8$)-cycloalkanolamine.

In certain embodiments of the invention, the cyclodextrin is a sulfoalkyl ether cyclodextrin derivative described in U.S. Pat. Nos. 5,134,127 or 5,376,645.

In certain embodiments of the invention, the compositions of the invention are useful for treatment of a condition amenable to treatment with topiramate, which include, e.g., the treatment of epilepsy, seizures (e.g., neonatal seizures), refractory status epilepticus, gambling, migraines, substance dependence, alcoholism; cocaine dependence, nicotine dependence, metabolic syndrome X; diabetes mellitus, type 2, vomiting, obsessive-compulsive disorder, refractory generalized social phobia, Tourette syndrome, levodopa-induced dyskinesia in Parkinson's Disease, refractory POS, Prader-Willi syndrome, multiple sclerosis, Lennox-Gastaut syndrome, Dravet's syndrome, bipolar disorder, obesity, post traumatic stress disorder, cluster headaches, severe headaches, anoxia (e.g., neonatal anoxia), and for any condition that can be treated with topiramate (e.g., for patients unable to take oral composition of topiramate).

The compositions of the invention are useful for providing neuroprotection for a patient (e.g., during surgery, e.g., during neonatal or pediatric surgery, e.g., during heart surgery or during a stroke, head injury, or coma).

In certain embodiments, the compositions are useful for protecting brain tissue near an area of ischemic stroke (the penumbra). The compositions can be administered, e.g., within a few hours after a stroke to protect the penumbra brain tissue from injury.

The compositions of the invention are also useful as a counter-measure for chemical warfare nerve agents such as sarin.

The compositions of the invention are also useful as an alternate treatment for a patient, e.g., as a bridge treatment during a period of time when a patient is not able to be treated with an oral formulation of topiramate.

The compositions of the invention are also useful for treating a patient who needs to rapidly attain or re-attain a pre-determined (i.e., targeted or desired) plasma topiramate concentrations, e.g., when those concentrations have declined as a result of not taking an oral formulation of topiramate. For example, in some embodiments the present invention is directed to providing a loading dose of topiramate, in which a dose of topiramate is parenterally administered to a patient to provide a predetermined blood systemic concentration of topiramate.

Generally, the compositions of the present invention can be administered to patients by various routes, including, but not limited to, subcutaneous, intravenous (including bolus injection), intramuscular, intraarterial, nasal, and rectal. Since administration of compositions of the present invention typically bypasses the patient's natural defenses against contaminants, the compositions are preferably sterile or capable of being sterilized prior to administration to a patient. Exemplary compositions therefore include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration to a patient. Further, transmucosal dosage forms, e.g., nasal or rectal, can be prepared for administration to a patient.

In some embodiments, the compositions of the present invention include one or more pharmaceutically acceptable excipients. The term "excipient," as used herein, refers to any inert substance that can be combined with topiramate and the sulfoalkyl ether cyclodextrin for preparing the compositions, including, for example, diluents, lubricants, colors, and the like.

Thus, the pharmaceutical dosage forms suitable for injection or infusion can include sterile aqueous solutions or dispersions or sterile powders comprising the active ingredient(s) which are adapted for the extemporaneous preparation of sterile injectable or infusible solutions or dispersions. The formulation can be provided as a stock solution, which is diluted with a liquid carrier composition such as dextrose, saline, plasma, or lactated Ringer's solution prior to administration to a patient. The formulation can be provided at a concentration of topiramate that is suitable for administration without dilution. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The formulation can further include a preservative, a solubilizing agent, an antioxidant, a buffering agent, an acidifying agent, a complexation enhancing agent, saline, dextrose, a lyophilizing aid (for example, bulking agents or stabilizing agents), an electrolyte, another therapeutic agent, an alkalizing agent, an antimicrobial agent, an antifungal agent, an antibacterial agent (e.g., a parabens or thimersol) or a combination thereof. Prolonged absorption of the injectable compositions (e.g., by IM injection) can be brought about by the use in the compositions of agents delaying or modifying the absorption, for example, aluminum monostearate, oleaginous vehicles, less soluble salt forms, or poloxamers (block copolymers). The pharmaceutical dosage forms suitable for injection or infusion can include sterile aqueous solutions or dispersions or sterile powders of topiramate which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, sulfoalkyl cyclodextrin in water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

In some embodiments, the compositions of the present invention are stable at about 25° C. for a period of at least 3 months, at least 6 months, at least 1 year, at least 1.5 years, at least 2 years, or at least 3 years. In some embodiments, the present invention provides a liquid topiramate composition comprising topiramate and a sulfoalkyl ether cyclodextrin, wherein the composition contains less than about 10% or less, about 5% or less, about 3% or less, about 2% or less, or about 1% or less of a topiramate degradant after storage at 25° C. for a period of at least 6 months, at least 1 year, at least 1.5 years, or at least 2 years. In some embodiments, the present invention provides a liquid topiramate composition comprising topiramate and a sulfoalkyl ether cyclodextrin, wherein the composition contains about 10% or less, about 5% or less, about 3% or less, about 2% or less, or about 1% or less of a topiramate degradant after storage at 40° C. for a period of at least 6 months, at least 1 year, at least 1.5 years, or at least 2 years.

In some embodiments, the composition further comprises pharmaceutically acceptable buffers and pH adjusting agents, wherein the pharmaceutical composition is adjusted in the pH range of about 4 to about 9, about 5 to about 8, or about 6 to about 7.5.

In some embodiments, the composition further comprises a sulfamic acid/sodium hydroxide buffer. In some embodiments, a sulfamic acid/sodium hydroxide buffer is present in a concentration of about 0.01 M to about 10 M, about 0.02 M to about 5 M, about 0.03 M to about 2 M, about 0.05 M to about 1 M, about 0.1 M to about 0.5 M, about 0.05 M, about 0.1 M, about 0.15 M, about 0.2 M, about 0.25 M, or about 0.3 M.

Sterile injectable solutions can be prepared by incorporating the active compound(s) into an appropriate solvent with the other optional ingredients enumerated herein, optionally followed by filter sterilization. In the case of sterile powders for the preparation of sterile injectable solutions, the preferred methods of preparation are spray drying, vacuum drying and the freeze drying techniques, which yield a powder of the active ingredient plus any additional desired ingredient present in the previously sterile-filtered solutions.

As used herein the terms "treat", "treating" and "treatment" include administering the composition prior to the onset of clinical symptoms of a disease state/condition so as to prevent the development of any symptom, as well as administering the composition after the onset of one or more clinical symptoms of a disease state/condition so as to reduce or eliminate any such symptom, aspect or characteristic of the disease state/condition. Such treating need not be absolute to be useful.

The term "therapeutically effective amount," as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

It has been found that a parenterally administered dose of topiramate is approximately equivalent in therapeutic efficacy to the same amount of topiramate administered orally. Thus, a therapeutically effective amount of topiramate that is parenterally administered to a patient in a composition of the present invention is approximately equivalent in efficacy to a similar topiramate dose that is orally administered. In some embodiments, a therapeutically effective amount of topiramate administered to a mammal is, e.g., an amount of about 25 mg to about 1 g/day. In some embodiments, a therapeutically effective amount of topiramate is about 0.2 mg/kg/day to about 50 mg/kg/day. In some embodiments, a therapeutically effective amount of topiramate is about 0.5 mg/kg/day to about 15 mg/kg/day, about 1 mg/kg/day to about 10 mg/kg/day, or about 1 mg/kg/day to about 5 mg/kg/day.

The compositions can, in certain embodiments, be provided in a unit dosage form or in a container from which a dose is measured out. As used herein the term "unit dosage form" relates to a composition containing a specific amount of a drug, the whole of which is intended to be administered as a single dose. It is distinguished from a supply of a multi-dose amount of a medicament, e.g., a bottle of medicine, from which a dose has to be measured out.

As used herein, the tet in "patient" is taken to mean warm blooded animals such as mammals, for example, non-humans such as cats, dogs, mice, guinea pigs, horses, bovine cows, and sheep, and humans.

In certain embodiments of the invention, treatment can include multiple doses, e.g., doses occurring over days, weeks, or years.

In some embodiments, a composition of the present invention further comprises at least one additional therapeutic agent (in addition to topiramate).

In certain embodiments of the invention, the compositions of the invention can be administered to neonatal, pediatric, adult, or geriatric patients. In some embodiments of the invention, the patient is a pediatric patient. As used herein, a "pediatric" patient is up to about 17 years of age, and includes neonates (0 to about 1 month of age), infants (about 1 month to about 2 years of age), children (about 2 to about 12 years of age) and adolescents (about 12 to about 17 years of age). In some embodiments of the invention, the patient is an adult patient. In some embodiments of the invention, the patient is a geriatric patient. Adult patients are at least about 18 years of age. Geriatric patients are at least about 65 years of age.

Topiramate

The compositions of the invention include topiramate (see, e.g., U.S. Pat. Nos. 6,949,518, 6,906,099, 6,699,840, 6,696,091 6,559,293, 6,503,884, 5,952,187, 5,258,402, and 4,513,006). Methods for preparing topiramate are known in the art. Topiramate is designated chemically as 2,3:4,5-di-O-isopropylidene-β-D-fructopyranose sulfamate and has the following Formula II:

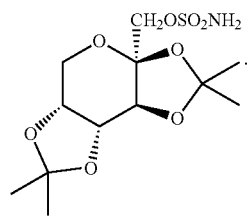

II

As used herein, the term "topiramate" refers to the above compound (2,3:4,5-di-O-isopropylidene-β-D-fructopyranose sulfamate), as well as pharmaceutically acceptable salts of topiramate, and polymorphs, solvates, hydrates, dehydrates, co-crystals, anhydrous, and amorphous forms thereof. The invention thus encompasses pharmaceutical compositions and dosage forms comprising pharmaceutically acceptable salts of topiramate, and polymorphs, solvates, hydrates, dehydrates, co-crystals, anhydrous, and amorphous forms of topiramate in combination with a sulfoalkyl ether cyclodextrin.

The Cyclodextrins

The compositions of the invention also include a cyclodextrin molecule (e.g., a sulfobutyl ether-β-cyclodextrin such as CAPTISOL® (CyDex Pharmaceuticals, Inc., Lenexa, Kans.), see, e.g., U.S. Pat. Nos. 6,133,248, 5,874,418, 6,046,177, 5,376,645, 5,134,127, 7,034,013, 6,869,939; Int'l Pat. Pub. No. WO2005/117911; and MSDS Number CAP-001). Methods for preparing a sulfobutyl ether-3-cyclodextrin are known in the art. The compositions comprising the sulfoalkyl ether cyclodextrin generally exhibit improved solubility, stability and/or bioavailability of topiramate.

CAPTISOL® cyclodextrin is a modified cyclodextrin. CAPTISOL® cyclodextrin is a polyanionic β-cyclodextrin derivative with a sodium sulfonate salt separated from the lipophilic cavity by a butyl ether spacer group, or sulfobutylether (SBE). CAPTISOL® cyclodextrin has been shown to be safe when administered parenterally, orally and via inhalation and does not exhibit the nephrotoxicity associated with β-cyclodextrin. Relative to β-cyclodextrin, CAPTISOL® sulfoalkyl ether cyclodextrin provides comparable or higher complexation characteristics and superior water solubility in excess of 90 g per 100 mL, a 50-fold improvement. CAPTISOL® sulfoalkyl ether cyclodextrin has the following Formula III:

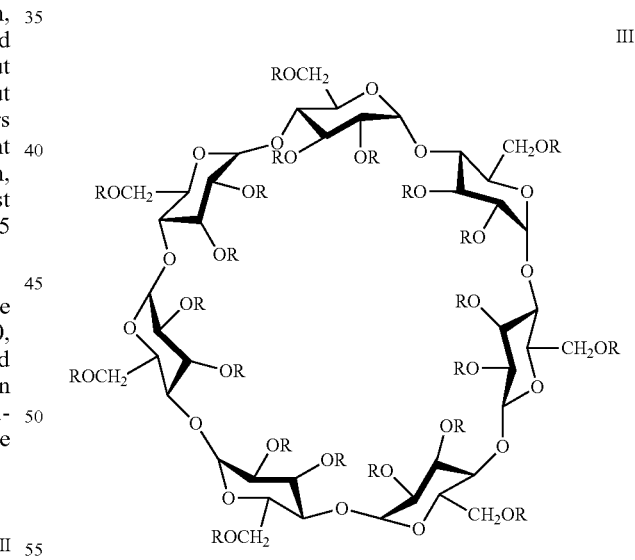

III where $R=(H)_{21-x}$ or $(-(CH_2)_4-SO_3Na)_x$. In certain embodiments, x=6.0-7.1.

The concentration of topiramate is, typically, e.g., about 5-100 mg/mL, e.g., 5-50 mg/mL, e.g., 10-20 mg/mL. In some embodiments of the invention, the cyclodextrin, such as a compound of Formula III, is present at a concentration of about 1-700 mg/mL.

In some embodiments of the invention, the sulfoalkyl ether cyclodextrin to topiramate mole ratio is about 0.01 to about 1.4. In some embodiments, sulfoalkyl ether cyclodextrin to topiramate mole ratio is about 0.05 to about 1.4, about 0.1 to about 1.4, about 0.5 to about 1.4, about 0.5 to about 1, about 1 to about 1.4, or about 1 to about 5. In some embodiments, the sulfoalkyl ether cyclodextrin to topiramate mole ratio is about 1.4 or greater. In some embodiments, the sulfoalkyl ether cyclodextrin to topiramate mole ratio is about 1.4 to about 5, about 1.4 to about 3, or about 1.4 to about 2. Based on the molecular weight for topiramate (339.36 g/mol) and the average molecular weight of the sulfoalkyl ether cyclodextrin of Formula III (2163 g/mol), a topiramate to sulfoalkyl ether cyclodextrin molar ratio of 1:1.4 is equivalent to a weight ratio of 1:8.9. Thus, in some embodiments a composition of the present invention comprises topiramate in a concentration of about 5 mg/mL to about 100 mg/mL and a sulfoalkyl ether cyclodextrin in a concentration of about 45 mg/mL to about 890 mg/mL, or topiramate in a concentration of about 5 mg/mL to about 50 mg/mL and a sulfoalkyl ether cyclodextrin in a concentration of about 45 mg/mL to about 450 mg/mL, or topiramate in a concentration of about 10 mg/mL to about 20 mg/mL and a sulfoalkyl ether cyclodextrin in a concentration of about 90 mg/mL to about 180 mg/mL.

The invention will now be illustrated by the following non-limiting Examples.

EXAMPLES

Example 1

Topiramate Phase Solubility Study

Figure 2:
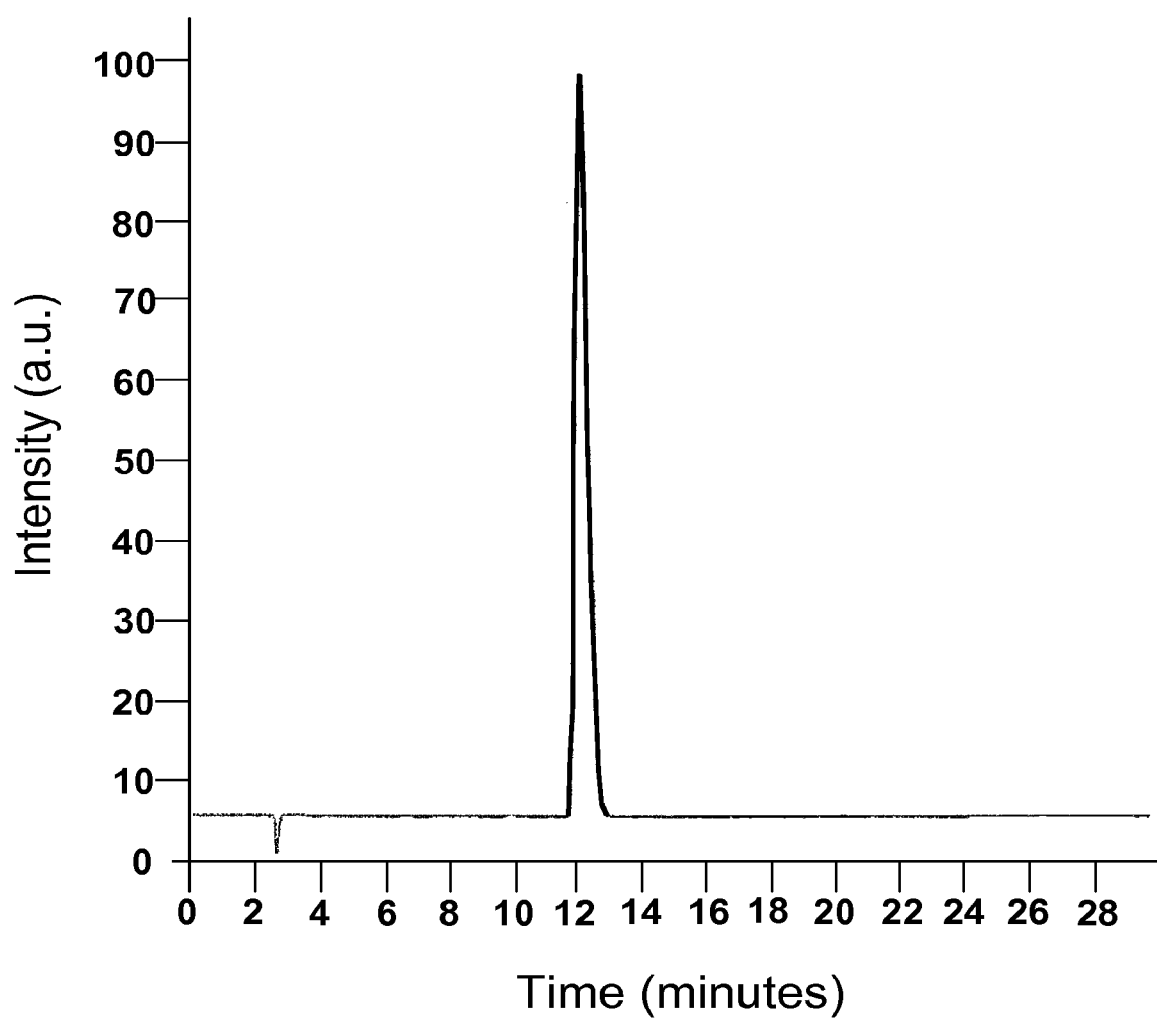
FIG. 2 depicts a chromatogram from injection of a topiramate standard.

A phase solubility study was conducted with the cyclodextrin CAPTISOL® and topiramate to evaluate the extent of solubilization of the drug by the derivatized cyclodextrin. An HPLC method was modified from the literature and shown to be linear over the range of interest. Chromatograms from injection of two of the topiramate standards are shown in FIGS. 1 and 2.

Figure 3:
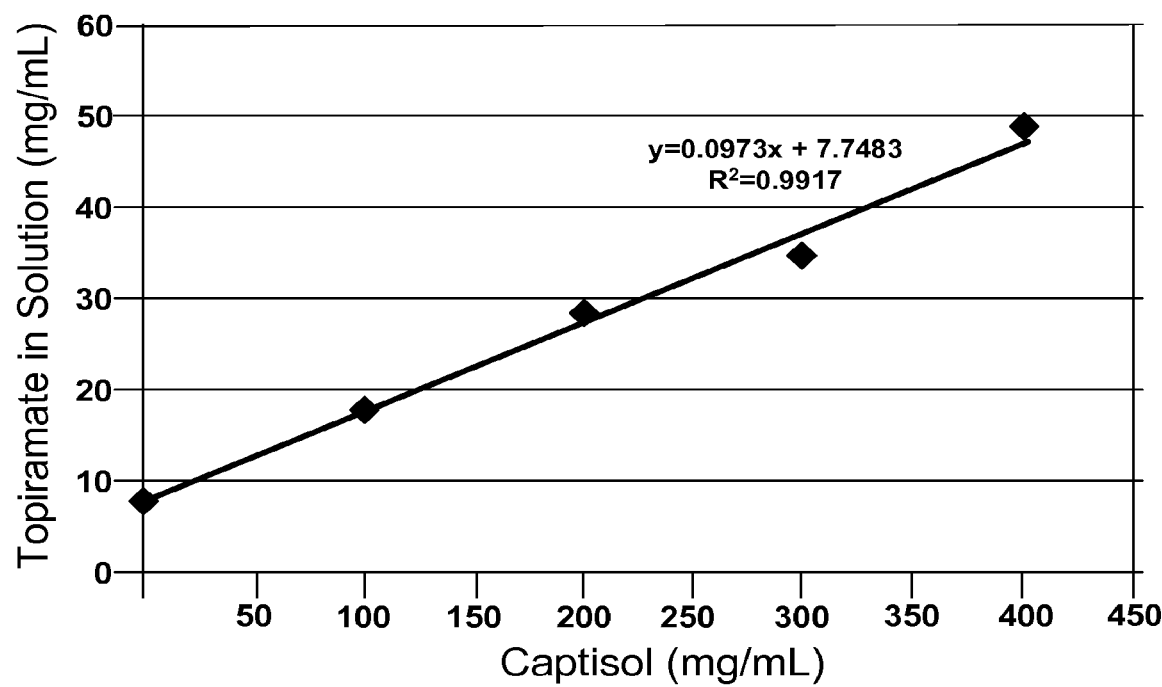
FIG. 3 provides a phase solubility diagram for topiramate in CAPTISOL® solutions (mg/mL), the results of which demonstrate that topiramate is well solubilized by the cyclodextrin CAPTISOL® in water.
Figure 4:
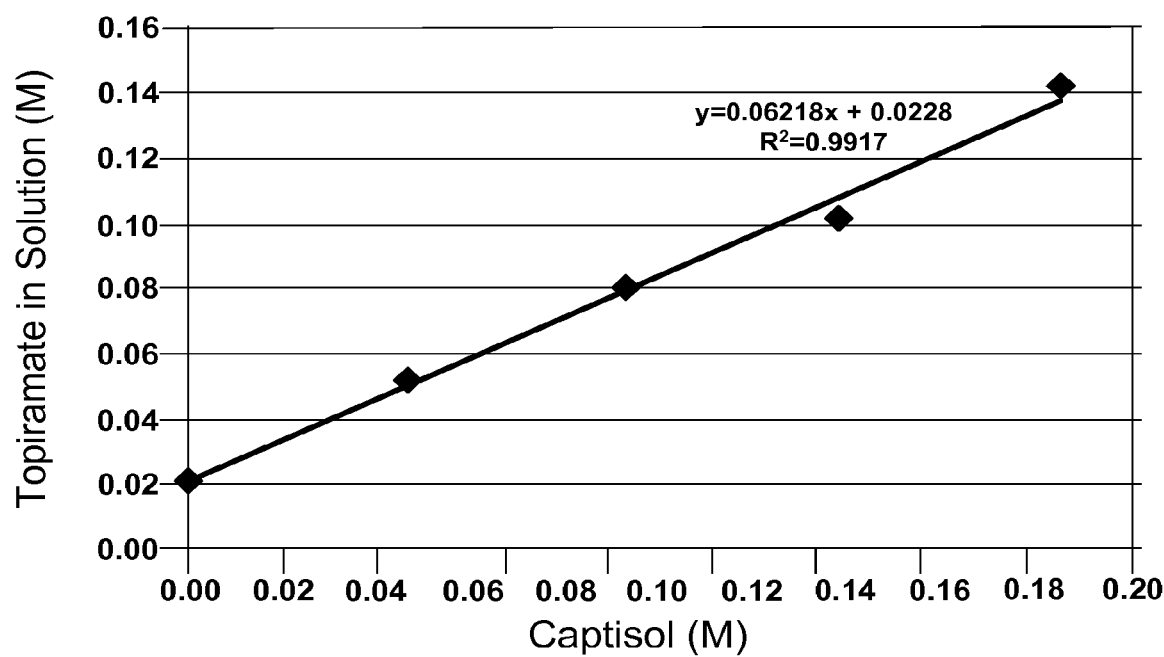
FIG. 4 provides a phase solubility diagram for topiramate in CAPTISOL® solutions (molar units), the results of which demonstrate that topiramate is well solubilized by the cyclodextrin CAPTISOL® in water.
Figure 5:
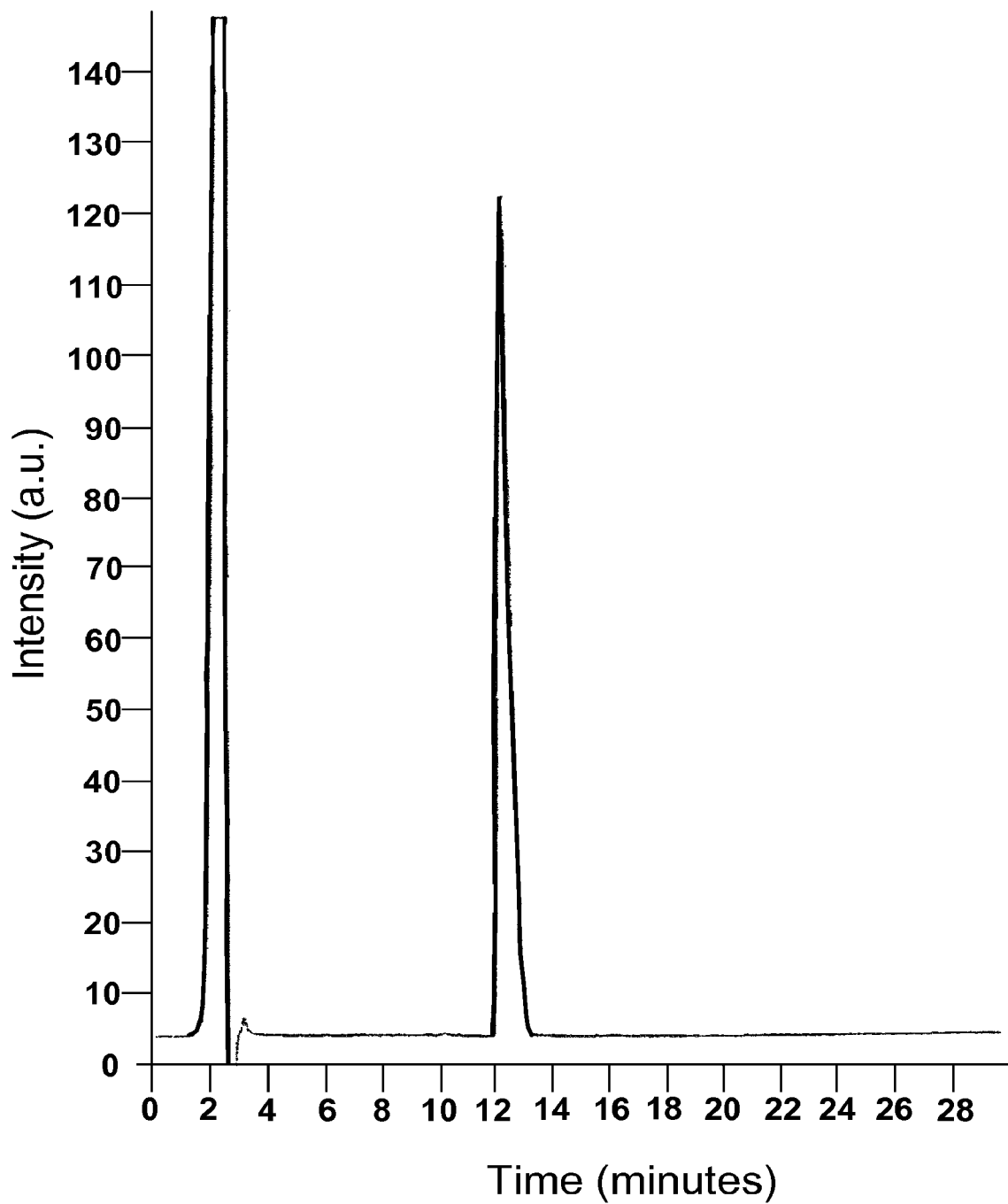
FIG. 5 depicts a chromatogram for the analysis of the solubility sample using 40% w/v the cyclodextrin CAPTISOL®.
Figure 6:
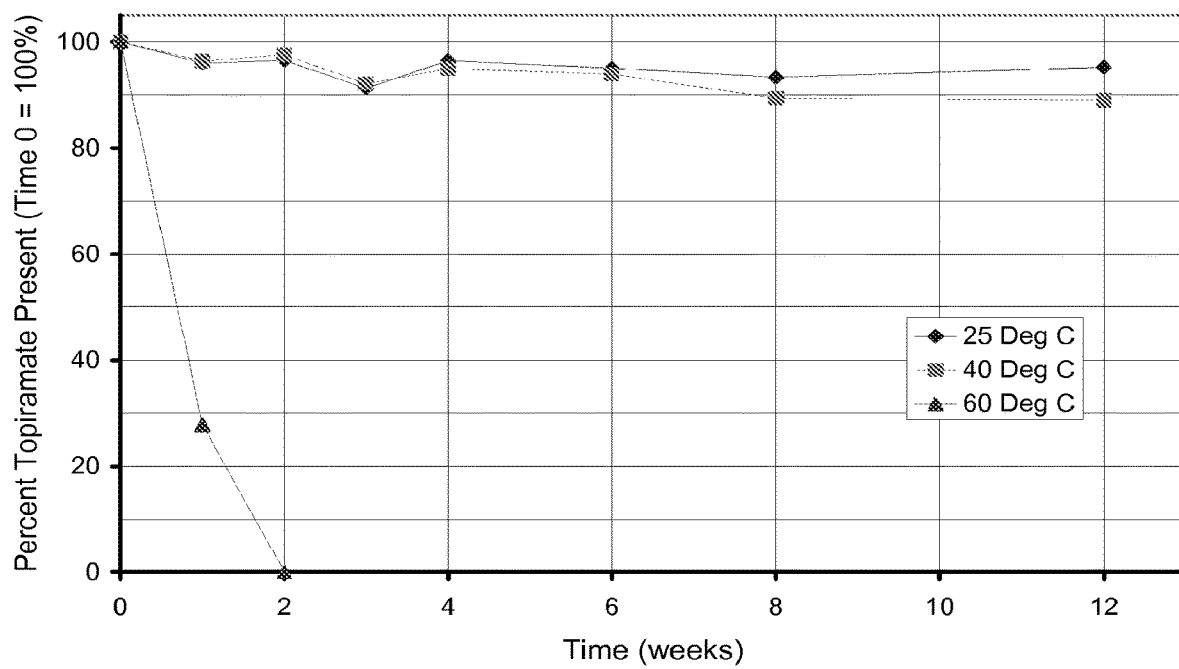
FIG. 6 provides a graphic representation of the stability of an aqueous 1% topiramate/10% CAPTISOL® (w/v) dosage form suitable for intravenous administration, and provides the observed percentage decrease in topiramate within the formulation as a function of time at 25° C., 45° C. and 60° C.

Results of the solubility study are illustrated in FIGS. 3 and 4 and show that topiramate is well solubilized by the cyclodextrin CAPTISOL® in water. Type A-linear phase solubility is observed and a binding constant of 71 $M^{-1}$ was calculated from the equation: $K_1:1=\text{slope}/S_0(1-\text{slope})$, where $S_0$ is the intrinsic solubility of the drug and "slope" is the slope of the molar plot of drug solubility versus cyclodextrin content. The magnitude of the calculated binding constant is low due to the drug being reasonably soluble in water in the absence of cyclodextrin (intrinsic solubility of 7.86 mg/mL). A chromatogram for the analysis of the solubility sample using 40% will of the cyclodextrin CAPTISOL® is given in FIG. 5.

Methods:

Solutions containing increasing amounts of dissolved CAPTISOL® brand of sulfobutylether-β-cyclodextrin were prepared and added to small glass vials. Excess solid topiramate was added to each vial and the vials were capped, vortexed and placed in constant agitation for five days at room temperature (about 23° C. to about 25° C.). If any vial showed complete dissolution of the added drug, additional drug was added and the vial returned to the stirring mode.

After the multi-day equilibration period, the vials were centrifuged (twice at 693×g, 25° C.) and aliquots were taken from the clear supernatant solutions. The aliquots were diluted 1:3 (1:5.67 for 40% cyclodextrin CAPTISOL® solutions) with mobile phase and analyzed by HPLC for topiramate content.

Materials:
Topiramate: Lot #LL-001-009-III-01 (Divi's Laboratories Ltd., Ameerpet, Hyderabad 500016, India).
The cyclodextrin CAPTISOL®, Lot #17CX01.HQ00009 (CYDEX, INC. Lenexa, Kans.).

Chromatography:
Chromatographic Conditions
HPLC: Dionex
Detection: Refractive Index Detector
Column: SB-Phenyl (5 μm) 250 mm×4.6 mm
Column Temperature: 35° C.
Mobile Phase: 40:60 (MeOH:Water)
Flow Rate: 1.0 mL/min isocratic
Run Time: 30 minutes
Sample Solvent: Mobile phase
Injection Volume: 50 μL
Retention Time: ~12.5 minutes Mobile Phase Preparation
Combined 400 mL of methanol and 600 mL of water, mixed well and filtered.

Standard Solutions
1—TPM10 Solution: ~250 mg of topiramate was weighed into a 25 mL volumetric flask, diluted to volume with mobile phase, and mixed well.
2—TPM5 Solution: 5 mL of TPM10 solution were transferred into a 10 mL volumetric flask and diluted to volume with mobile phase.
3—TPM1 Solution: 1 mL of TPM10 solution was transferred into a 10 mL volumetric flask and diluted to volume with mobile phase.

Example 2

Preparation and Verification of $[^{13}C]_6$-Topiramate

Isotopically labeled topiramate ($[^{13}C]_6$-TPM) was synthesized by Isotech Laboratories, Inc. Quantitative identification of the stable-isotope topiramate was performed by Isotech Laboratories, Inc. using $^1$H-NMR, $^{13}$C-NMR, and mass spectrometry. The $[^{13}C]_6$-TPM was then to the University of Minnesota for further quantitative analysis by liquid chromatography/mass spectrometry (LC/MS).

The LC/MS procedure was as follows: 25 mg $[^{13}C]_6$-TPM was weighed on a Cahn electrobalance, transferred into a 2 dram vial, and dissolved in 2.5 mL of 10% w/v CAPTISOL® aqueous solution. The 10% w/v CAPTISOL® aqueous solution was prepared by weighing 10 g of CAPTISOL® (adjusted for water content) and dissolving it in 100 mL of water. Reference unlabeled topiramate (obtained from Sigma-Aldrich Co. or Toronto Research Chemicals, Inc.) was prepared in an identical fashion. Separation of topiramate was performed using reverse phase chromatography, and detection used electrospray ionization (ESI) in negative-scan mode. Five replicate 0.02 mL injections were run for both the $[^{13}C]_6$-TPM and the non-isotopically labeled reference standard. The chromatographic conditions consisted of a mobile phase of 50% methanol and 50% ammonium acetate buffer (~pH 6.9). The flow rate was 0.5 mL/min and the column packing material was 3.5 μm particle size reverse-phase ZORBAX® XDB(C8) (E. I. Du Pont de Nemours and Co.) in a column of 150 mm length×3.0 mm I.D. Isotopic purity was determined by scanning from 50 m/z to 500 m/z for 30 minutes. Measuring the relative abundance of the ions at 339 m/z and quantitative estimates of content was done by direct comparison of the mean peak area ratios of $[^{13}C]_6$-TPM and the internal standard deuterated topiramate ("TPM-d12") with the topiramate reference.

After verification, the stable-isotope topiramate was sent to the University of Iowa for formulation of the parenteral product with sulfoalkyl ether cyclodextrin.

Example 3

Formulation of [$^{13}$C]$_6$-TPM with Sulfoalkyl Ether Cyclodextrin

The stable-isotope topiramate was sent in sealed containers from University of Minnesota to the Pharmaceutical Service Division, College of Pharmacy, University of Iowa, Iowa City, Iowa 52242, for formulation into a parenteral solution suitable for administration into humans.

The stable-isotope topiramate was formulated with CAPTISOL® for intravenous administration. The resulting composition contained 1% w/v topiramate and 10% w/v CAPTISOL®. The manufacturing procedure was as follows:
1) 200 g of CAPTISOL® (adjusted for water content) was dissolved in 2.0 L of deionized sterile water to generate a 10% w/v CAPTISOL® solution;
2) 20 g of [$^{13}$C]$_6$-TPM was added to the 10% w/v CAPTISOL® solution;
3) The solution was stirred for 24 hours at room temperature;
4) Ampoules were sterilized in preparation for filling;
5) All equipment to be used was prepared and sterilized;
6) The solution was transferred to a class 100 clean room for sterile filtration;
7) Before, during and after the transfer, the filling area was monitored for viable flora;
8) The solution was sterile filtered through a 0.22 μm DURAPORE® (Millipore Corp.) filter into a sterile receiver in a class 100 area;
9) At the end of the filtration the integrity of the filter was tested;
10) The ampoules were then filled and sealed under a nitrogen flush; and
11) The ampoules were stored at 2° C. to 8° C. prior to administration.

Example 4

Stability of [$^{13}$C]$_6$-TPM/CAPTISOL® Formulation

Topiramate 10 mg/mL in 10% CAPTISOL® is stable in solution. The stability of topiramate in 10% CAPTISOL® was analyzed at 25° C., 40° C., and 60° C. The results are presented in the following Table.

TABLE

Stability of 10 mg/mL topiramate in 10% CAPTISOL ®.

| Temperature | Weeks | | | | | | | |
|---|---|---|---|---|---|---|---|---|
| | 0 | 1 | 2 | 3 | 4 | 6 | 8 | 12 |
| 25° C. | 10.6 | 10.2 | 10.2 | 9.7 | 10.2 | 10.1 | 9.9 | 10.1 |
| 40° C. | 10.6 | 10.2 | 10.4 | 9.8 | 10.1 | 10.0 | 9.5 | 9.5 |
| 60° C. | 10.6 | 2.9 | — | — | — | — | — | — |

These results indicate the [$^{13}$C]$_6$-TPM/CAPTISOL® solution retains its stability for at least 12 weeks after formulation when stored at 25° C. Ampoules containing the topiramate/Captisol® solution are stored at 2° C. to 8° C.

Example 5

Dosing of Adult Subjects with the [$'^{13}$C]$_6$-TPM/CAPTISOL® Formulation

A. Subject Availability and Recruitment

Subjects were recruited from the MINCEP Epilepsy Care, Fairview University Medical Center, and epilepsy and migraine clinics in Minneapolis and St. Paul, Minn.

B. Study Design

This was an open labeled, single dose study in adult patients on a maintenance dose of topiramate for treatment of either migraines or epilepsy.

C. Inclusion Criteria:

Patients were recruited using the following screening criteria: Persons taking topiramate as either AED monotherapy or with other non-interacting AEDs and on a stable oral topiramate dose for at least two weeks. All patients were 18 years of age and older.

D. Exclusion Criteria:

The following criteria was used to eliminate patients from the study: patients who were pregnant; patients who were breast feeding; patients with significant medical problems who may not tolerate intravenous administration; patients taking medications known to affect topiramate disposition (i.e., patients taking AEDs including phenobarbital, primidone, oxcarbazepine, phenytoin, and carbamazepine; patients taking rifampin, St. John's wort, efavirenz; patients taking SSRIs including fluoxetine, fluvoxamine, sertraline, and paroxetine; patients taking Calcium Channel Blockers including diltiazem and verapamil; patients taking Macrolide Antibiotics including clarithromycin, erthromycin, spiramycin, and troleandomycin; and patients taking cimetidine, denzimol, ketoconazole, nefazodone, isoniazid, propoxyphene, itraconazole, fluconazole, grapefruit juice, ritonavir, indinavir, nelfinavir, delavirdine and amprenavir.

The research coordinator contacted patients meeting the inclusion/exclusion criteria, explained the study, and obtained informed consent. The research coordinator also scheduled subjects for admission to the General Clinical Research Center where the study was conducted.

E. Protocol

Patients were instructed to take their evening topiramate dose the day before the study, then fast until after administration of study drug. On the day of the study, subjects were admitted to University of Minnesota General Clinical Research Center where a neurologist performed a brief physical and neurological exam, vital signs were recorded, an ECG strip was obtained, indwelling catheters were placed in the left and right forearms, and blood samples were drawn for baseline laboratory tests.

Prior to infusing intravenous topiramate, a medication history and compliance was determined, and a seizure history for the last six months was obtained and categorized as: 0=seizure free, 1=an average of <1 seizure/month, 2=an average of >1 seizure/month.

A baseline assessment of topiramate toxicity was performed using the following criteria: ataxia and nystagmus: 0=none, 1=mild, 2=severe. As used herein, "ataxia" is classified as "mild"—for unsteady with tandem gait testing, but able to perform without assistance, or as "severe"—unable to perform tandem gait testing without assistance As used herein, "nystagmus" is classified as "mild"—present on extreme gaze, or as "severe"—present on midline gaze.

The $[^{13}C]_6$-TPM was administered into the right arm catheter, while blood samples for laboratory tests were drawn from the left arm. Laboratory chemistries included albumin, blood chemistries, kidney and liver function test, and genotyping for drug disposition. A 25 mg $[^{13}C]_6$-TPM dose was then infused over 10-20 minutes. The exact dose administered was determined gravimetrically from the pre- and post-dose syringe weights. At the end of the infusion, patients took their prescribed oral morning dose; thereafter they resumed their regular dosing regimen. Blood samples for pharmacokinetic analysis were taken at 0, 5 minutes, 15 minutes, 30 minutes, 1 hour, 2 hours, 4 hours, 6 hours, 10 hours, 24 hours, 48 hours, 72 hours and 96 hours after intravenous administration of the topiramate. Urine was collected from 0-24 hours for analysis of the parent drug to determine renal clearance. Urine volumes were measured and 15 mL aliquots were stored at −80° C. until analysis.

Patients were discharged from the research center following collection of a 12- or 24-hour sample. Subsequent blood samples were collected on an outpatient basis.

F. Analytical Methods

For plasma assays, standard curves containing six different concentrations that include the concentrations in the established therapeutic range were processed by addition of labeled and unlabeled parent drug to blank plasma. Extraction and derivatization procedures are described below. All samples from an individual patient were run at the same time along with a complete standard curve and quality control samples that cover the therapeutic range of the respective drug being measured. Standard curves (peak area ratio vs. concentration) were processed by a weighted linear regression (weight=1/estimated total variance at each concentration) or best fit.

Topiramate was detected using a LC/MS method employing the electrospray ionization (ESI) and negative scan mode. This method is designed to measure both unlabeled topiramate and the stable-isotope topiramate using a negative ESI and SIM mode of liquid chromatograph mass spectrometer. The analytes were separated using ZORBAX® LC8/LC18 and a mobile phase consisting of ammonium acetate buffer and methanol. The data generated using CHEMSTATION® software (Agilent) and quantified using deuterated topiramate ("TPM-d12", internal standard). Patient samples were run along with a 7-concentration standard curve (run in triplicate) and nine quality control samples (low, med and high also run in triplicates), analyzed in human plasma using liquid extraction with methyl-tert-butylether and negative ion electrospray mass spectrometry. The quantitative analysis was performed using selective ion monitoring mode for topiramate at m/z=338 and m/z=350 for TPM-d12 in the negative mode. The unlabeled topiramate calibration curve ranged from 0.05 μg/mL to 10 μg/mL.

G. Pharmacokinetics Analysis

Both stable-isotope topiramate and non-labeled topiramate concentration-time data was analyzed by non-compartmental methods to obtain AUC, clearance, half-life, and volume of distribution data. The AUC was determined by the trapezoidal rule and the terminal half-life was determined by linear regression of the terminal phase on log concentration vs. time plots. WINNONLIN® (Tripos L.L.P.), a pharmacokinetic data analysis package was used to fit the data to standard pharmacokinetic models (one and two-compartment models).

H. Stable-Isotope Pharmacokinetic Calculations:

Elimination rate constant ($k_{el}$): $k_{el}$ was determined by the best fit of the post-infusion isotope concentration-time data.

Area Under the Isotope Concentration-time Curve (AUC$_{iso}$): AUC$_{iso}$ was calculated from zero time to infinity using the trapezoidal method for the area from zero to 96 hours while the terminal portion of the AUC was determined by dividing the last measurable serum isotope concentration by $k_{el}$.

$$AUC_{iso}=AUC_0\text{–}96\text{ hrs}+C_p96\text{ hrs/kel}$$

Distribution Volume at Steady State ($V_{dss}$): $V_{dss}$ was determined as follows:

$$V_{dss}=Dose_{iso}*AUMC/AUC$$

where AUMC is the area under the first moment curve, and calculated by determining the area under the curve of a plot of the product of concentration and time versus time from zero time to infinity.

Clearance ($Cl_{iso}$): Clearance following the intravenous administration of the stable-isotope was calculated by the following equation:

$$Cl_{iso}=Dose_{iso}/AUC_{iso}$$

I. Non-Isotope Pharmacokinetic Calculations

Area Under the Concentration-time Curve following of oral dose (AUC$_{oral}$): The AUC$_{oral}$ over the dosing interval (either 12 or 24 hours) was determined by the trapezoidal method.

Bioavailability (F): The fraction (F) of the orally administered dose that is absorbed was determined by comparing the AUC$_{oral}$ with the AUC as shown below. AUC$_{iso}$ was adjusted for dose.

$$F=AUC_{oral} \text{ (over dosing interval)}/AUC_{iso}\times(IV\text{ dose}/Oral\text{ dose})$$

The AUC following an initial dose is equal to the AUC over a dosing interval at steady state. Under first order conditions, the AUC$_{iso}$ was adjusted to reflect the area following the oral dose.

Total Clearance ($C_{tot}$) and Unbound Clearance ($Cl_{unb}$): $Cl_{tot}$ and $Cl_{unb}$ were determined by correcting for the fraction of dose absorbed as follows:

$$Cl_{tot}=Oral\text{ dose}*F/AUC_{oral}\text{ (over dosing interval)}$$

$$Cl_{unb}=Cl_{tot}/FF=Oral\text{ dose}*F/FF*AUC_{oral}\text{ (over dosing interval)}$$

J. NONMEM Analysis of Pharmacokinetics and Pharmacodynamics

Age-related changes in clearance can also be modeled using a nonlinear mixed-effects modeling pharmacokinetic/statistical program (NONMEM). This approach is designed to allow the pharmacokinetics to be evaluated from a population perspective, and in doing so, models for the influence of various covariates on the pharmacokinetic parameters can be proposed and tested. Thus, a population-based model for age-related changes in topiramate clearance can be developed. In addition, the effect of, e.g., sex, race, and genotype on clearance, independent from the effect due to age, can be determined.

K. Results

Ten subjects (9 females, 1 male) have completed the study since enrollment began in August, 2008. An additional 10 subjects will be enrolled within the next 12 months.

Complete results are available for three (3) subjects (designated as TUMN1, TUMN2 and TUMN3) and are reported in the following Table. Detailed data on blood pressure and heart rates by subject (data not shown) was also collected.

TABLE

Pharmacokinetic and Safety Results following Intravenous Administration of Topiramate

|  | TUMN1 | TUMN2 | TUMN3 |
|---|---|---|---|
| Oral dose | 50 mg b.i.d. | 100 mg q.d. | 25 mg b.i.d. |
| IV dose | 25 mg | 25 mg | 25 mg |
| Clearance (L/hr) | 1.01 | 1.07 | 1.11 |
| Distribution volume (L/kg) | 0.78 | 0.68 | 0.70 |
| Half life (hrs) | 30.5 | 28.4 | 38.0 |
| Bioavailability (%) | 102% | 106% | 109% |
| BP changes | None | None | None |
| Pulse changes | None | None | None |
| EKG changes | None | None | None |
| Injection site irritation | None | None | None |
| Other adverse events | None | None | Vasovagal response during IV line placement |

Figure 7:
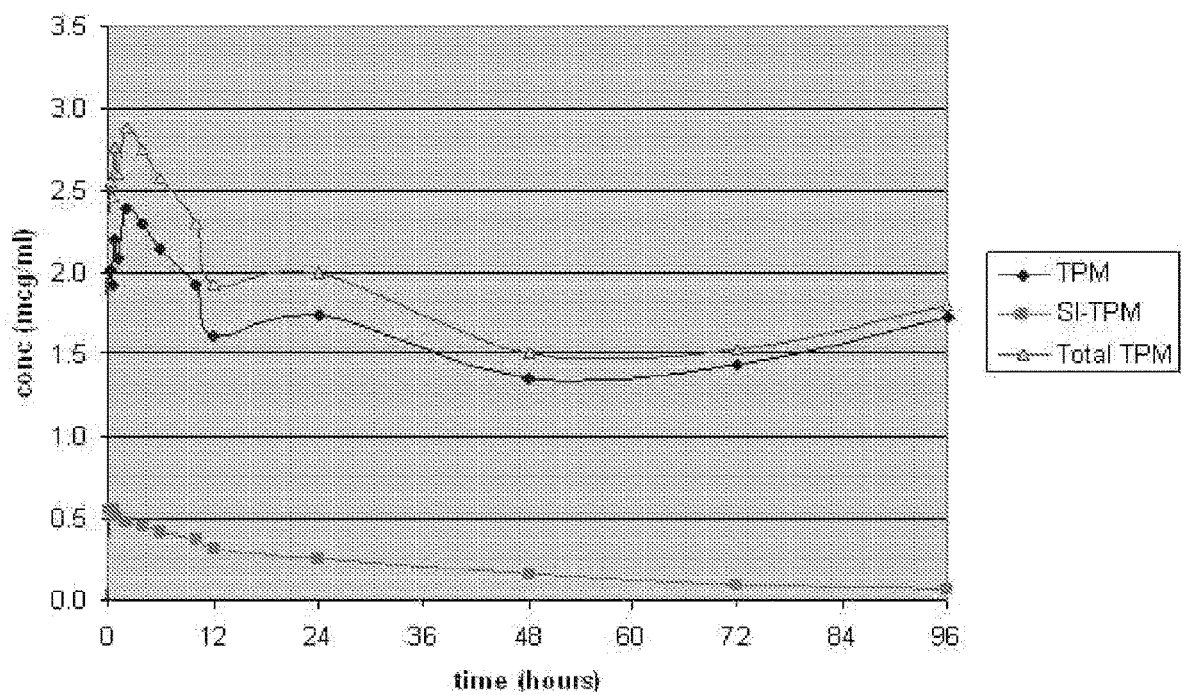
FIGS. 7-9 provide graphic representations of in vivo pharmacokinetics of topiramate and stable, isotopically labeled topiramate after intravenous administration of the stable, isotopically labeled topiramate to adult patients.
Figure 8:
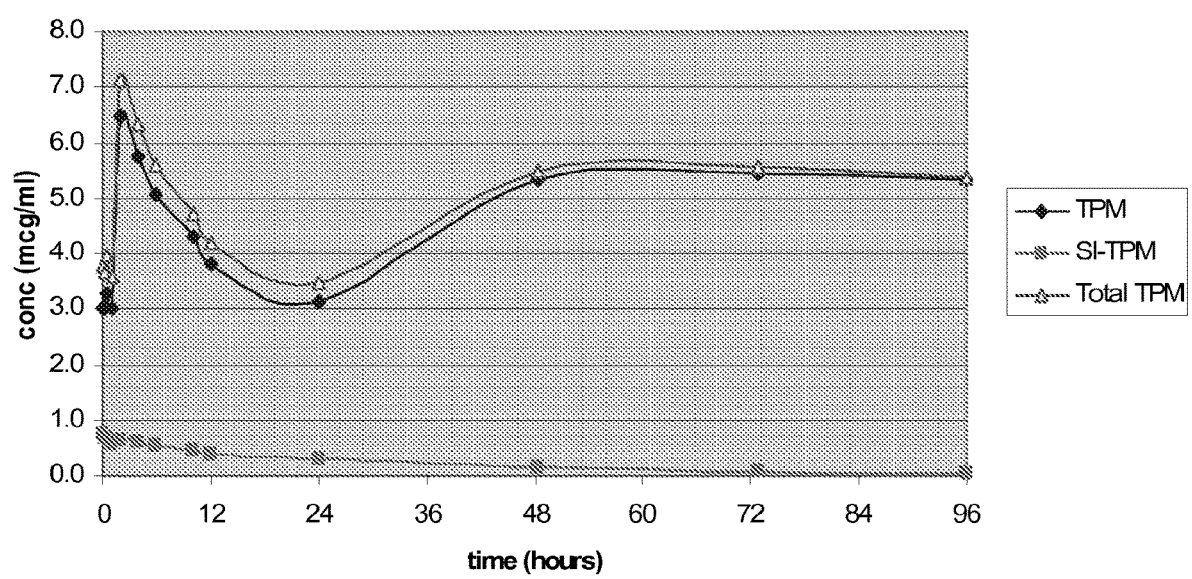
Figure 9:
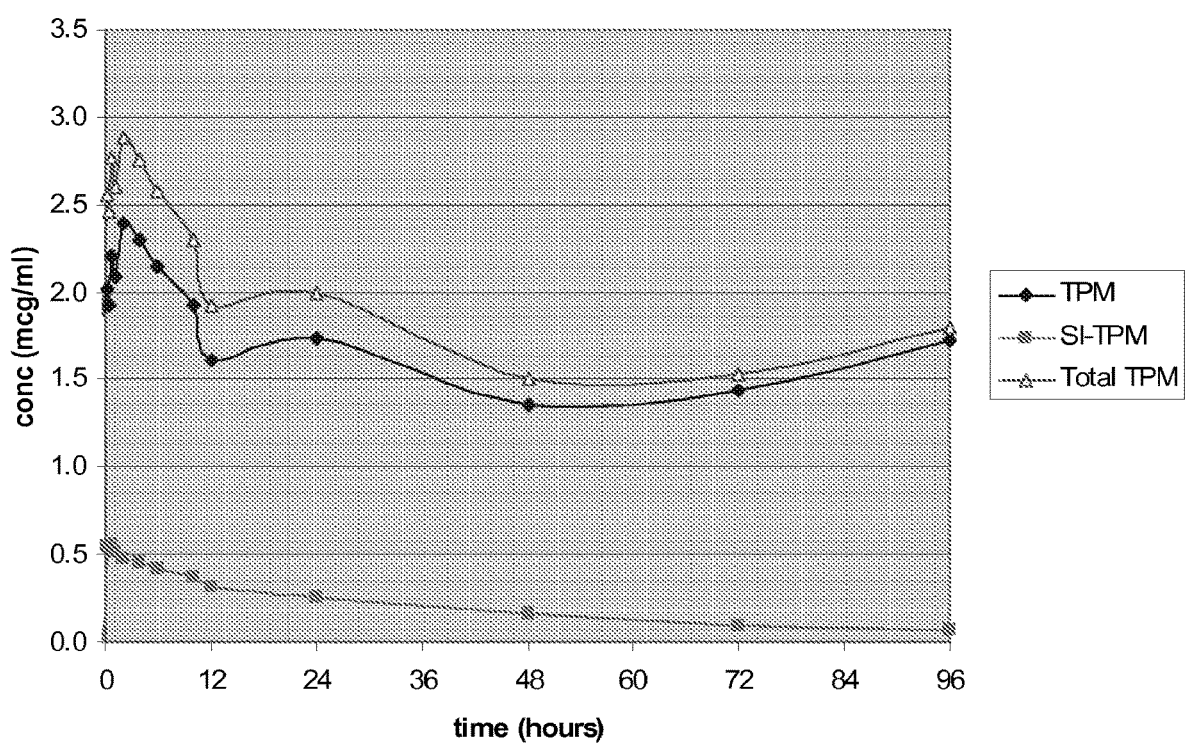

Plots of the concentration-time profiles for the stable-isotope topiramate ("SI-TPM"), topiramate ("TPM"), and the combination of SI-TPM and TPM are shown for each subject in FIGS. 7-9. Referring to FIGS. 7-9, the data shows that the SI-TPM exhibits pharmacokinetic parameters similar to orally dosed topiramate.

The results provide information regarding the pharmacokinetic parameters and bioavailability for intravenously-administered topiramate that can be used to optimize therapy when an intravenous formulation of topiramate is administered. First, the determination that the oral absorption is approximately 100% indicates that patients should be given the same dose intravenous dose as would be administered orally. Second, the extended elimination half-life of the intravenously administered topiramate indicates that an intravenous dosage can be administered twice daily without adverse effects. Third, the distribution volume for intravenously administered topiramate of approximately 0.7 L/kg provides a means to quickly and safely attain a desired drug concentration that should be administered intravenously as a loading dose ("LD"). The equation for determining the appropriate loading dose base on a subject's mass is as follows:

LD=Target [TPM conc.]×(Distribution Volume)×(Subject Mass(kg))

As an example, if a patient has an in vivo topiramate concentration of zero prior to administration of a loading dose, and the desired concentration is 10 mg/L, then the intravenously-administered topiramate loading dose is:

LD=(10 mg/L)×(0.7 L/kg)×SM(kg)

where "SM(kg)" is the subject's mass in kilograms. Thus, for a subject having a body mass of 80 kg, a loading dose of 560 mg is appropriate.

Example 6

Topiramate/CAPTISOL® Formulations

Topiramate was formulated with and without a sulfoalkyl ether cyclodextrin solubilizing agent in either phosphate or sulfamic acid/sodium hydroxide buffer using a procedure analogous to that described in Example 3. Formulations A, B, C and F, which contain a sulfoalkyl ether cyclodextrin were prepared. Formulations D and E were also prepared, which did not contain a sulfoalkyl ether cyclodextrin. Formulations A-F are listed in the following Table.

TABLE

Formulations A-F, which comprise topiramate, a phosphate or sulfamic acid buffer, and optionally and CAPTISOL ®.

| | | Formulation | | | | |
|---|---|---|---|---|---|---|
| Ref. | Topiramate | SAE-CD$^a$ | Buffer | Buffer Conc. | pH | Additional Excipient |
| A | 35 mg/mL | 35% w/v | Phosphate | 0.1M | 7.5 | — |
| B | 35 mg/mL | 35% w/v | Sulfamic Acid/NaOH | 0.05M | 7.5 | — |
| C | 35 mg/mL | 35% w/v | Sulfamic Acid/NaOH | 0.1M | 7.5 | — |
| D | 7 mg/mL | — | Phosphate | 0.1M | 7 | — |
| E | 7 mg/mL | — | Phosphate | 0.1M | 8 | — |
| F | 35 mg/mL | 35% w/v | Phosphate | 0.1M | 7.5 | PEG 400 (20% v/v) |

$^a$CAPTISOL ® (CyDex Pharmaceuticals, Inc., Lenexa, KS).

Example 7

Formulation Stability

Formulations A-F, described in Example 6, were stored at 5° C., 25° C., 40° C., 50° C. and 60° C. for a period of six to twelve weeks. The stability of each formulation was tested at 1 or 2 week intervals to determine the assay of topiramate ("TPM") and the primary degradant, bis-O-(isopropylidene)-fructopyranose ("RCA"). It has been suggested that topiramate degrades via two possible pathways. See, e.g., A. Klockow-Beck et al., *J. Chromatogr. B* 720:141 (1998).

The stability data for Formulations A-F was then plotted as a function of temperature, and using the Arrhenius equation, the 1.5-year and 2-year stability of each formulation at 5° C. and 25° C. was extrapolated. The Arrhenius equation gives the dependence of the rate constant (k) for a chemical reaction on the temperature (T) and activation energy ($E_a$), as follows:

$$k = Ae^{\frac{-E_a}{RT}}$$

where A is the pre-exponential factor and R is the gas constant. Rewritten, the Arrhenius equation provides a method to extrapolate the rate constant as a function of temperature, as follows:

$$\ln k = \ln A - \frac{E_a}{R}\left(\frac{1}{T}\right)$$

where a plot of ln k versus 1/T provides a y-axis intercept of ln A and a slope of $E_a/R$. A plot of the stability data obtained at 40° C., 50° C. and 60° C. (data not shown) provided the theoretical yield of RCA after 1.5-year and 2-years, which was used to estimate the overall stability yields for Formulations A-F. The results of this analysis are provided in the following Table.

TABLE

Extrapolated stability data for Formulations A-F at 5° C. and 25° C. for 1.5 years and 2 years, wherein the RCA concentrations are based on data from Arrhenius plots of stability data measured for Formulations A-F at 40° C., 50° C. and 60° C. at 6-12 weeks.

| Ref. | Data Points used in Analysis | Last Time Point collected | Temp (° C.) | RCA @ t = 1.5 yrs | RCA @ t = 2 yrs | $t_{90}$ (1.5 yr.)$^a$ | $t_{90}$ (2 yr.)$^a$ |
|---|---|---|---|---|---|---|---|
| A | 6-60° C.<br>6-50° C.<br>6-40° C. | 12 weeks | 5° C.<br>25° C. | 0.07%<br>1.33% | 0.07%<br>1.77% | PASS<br>PASS | PASS<br>PASS |
| B | 3-60° C.<br>5-50° C.<br>6-40° C. | 6 weeks | 5° C.<br>25° C. | 0.08%<br>0.56% | 0.08%<br>0.71% | PASS<br>PASS | PASS<br>PASS |
| C | 3-60° C.<br>5-50° C.<br>6-40° C. | 6 weeks | 5° C.<br>25° C. | 0.10%<br>0.81% | 0.10%<br>1.05% | PASS<br>PASS | PASS<br>PASS |
| D | 6-60° C.<br>6-50° C.<br>8-40° C. | 12 weeks | 5° C.<br>25° C. | 0.72%<br>13.10% | 0.91%<br>17.43% | PASS<br>FAIL | PASS<br>FAIL |
| E | 6-60° C.<br>6-50° C.<br>8-40° C. | 12 weeks | 5° C.<br>25° C. | 0.45%<br>10.74% | 0.60%<br>14.32% | PASS<br>FAIL | PASS<br>FAIL |
| F | 3-60° C.<br>5-50° C.<br>5-40° C. | 6 weeks | 5° C.<br>25° C. | 0.13%<br>0.96% | 0.14%<br>1.24% | PASS<br>PASS | PASS<br>PASS |

$^a$The "PASS" or "FAIL" rating is based on the stability of topiramate having at least a 90% recovery at 1.5 years and 2 years, respectively.

The above data indicates that liquid topiramate compositions that do not contain a sulfoalkyl ether cyclodextrin (such as Formulations D and E) are not likely to be stable at room temperature for extended periods of time (e.g., 1.5-2 years), and would likely require refrigeration and/or lyophilization to enhance stability for storage of such duration.

The above data also indicates that liquid topiramate compositions that contain a sulfoalkyl ether cyclodextrin (Formulations A-C and F) are likely to be stable at room temperature for an extended period of time. Furthermore, liquid topiramate compositions that contain a sulfoalkyl ether cyclodextrin and a sulfamic acid/sodium hydroxide buffer (Formulations B and C) exhibit the highest long-term stability, and therefore can be stored at room temperature for extended periods of time. Thus, in some embodiments the present invention is directed to a composition comprising topiramate and a sulfoalkyl ether cyclodextrin that is stable at room temperature (about 25° C.) for a period of at least 1.5 years, or at least 2 years.

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

It is to be appreciated that the Detailed Description section, and not the Summary and Abstract sections, is intended to be used to interpret the claims. The Summary and Abstract sections can set forth one or more, but not all exemplary embodiments of the present invention as contemplated by the inventor(s), and thus, are not intended to limit the present invention and the appended claims in any way.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. No language in the specification should be construed as indicating any non-claimed element as essential to the practice of the invention.

The invention includes combinations and sub-combinations of the various aspects and embodiments disclosed herein. These and other aspects of this invention will be apparent upon reference to the following detailed description, examples, claims and attached figures.

What is claimed is:

1. A method of treating a subject having a condition selected from the group consisting of epilepsy, seizures, anoxia, stroke, status epilepticus, refractory status epilepticus, gambling addiction, migraines, substance dependence, alcoholism, cocaine dependence, nicotine dependence, metabolic syndrome X, diabetes mellitus type 2, vomiting, obsessive-compulsive disorder, refractory generalized social phobia, Tourette syndrome, levodopa-induced dyskinesia in Parkinson's Disease, refractory POS, Prader-Willi syndrome, multiple sclerosis, Lennox-Gastaut syndrome, Dravet's syndrome, bipolar disorder, obesity, post-traumatic stress disorder, cluster headaches, severe headaches, conditions caused by exposure to a chemical warfare nerve agent, hypoxic-ischemic encephalopathy, subdural hematoma, periventricular leukomalacia, mental retardation, grey matter injury, white matter injury, and an infection, wherein the treatment consists of administering to a subject in need thereof an effective amount of a composition consisting of topiramate or a salt thereof, one or more pharmaceutically acceptable carriers, and a compound of Formula (I):

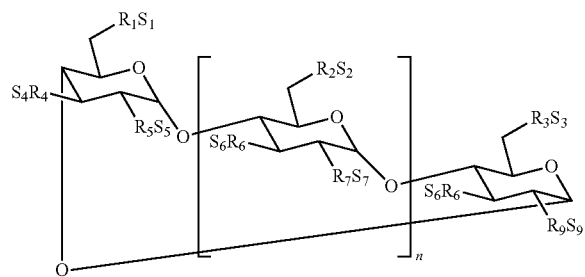

(I)

wherein: n is 4, 5 or 6; $R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$ and $S_9$ are each, independently, H or a pharmaceutically acceptable cation.

2. The method of claim 1, wherein the administration is parenteral.

3. A method of treating a subject having a condition selected from the group consisting of epilepsy, seizures, anoxia, stroke, status epilepticus, refractory status epilepticus, gambling addiction, migraines, substance dependence, alcoholism, cocaine dependence, nicotine dependence, metabolic syndrome X, diabetes mellitus type 2, vomiting, obsessive-compulsive disorder, refractory generalized social phobia, Tourette syndrome, levodopa-induced dyskinesia in Parkinson's Disease, refractory POS, Prader-Willi syndrome, multiple sclerosis, Lennox-Gastaut syndrome, Dravet's syndrome, bipolar disorder, obesity, post-traumatic stress disorder, cluster headaches, severe headaches, conditions caused by exposure to a chemical warfare nerve agent, hypoxic-ischemic encephalopathy, subdural hematoma, periventricular leukomalacia, mental retardation, grey matter injury, white matter injury, and an infection, the method consists of administering to a subject in need thereof an effective amount of a composition consisting of topiramate or a salt thereof, one or more pharmaceutically acceptable carriers, and a compound of Formula (III):

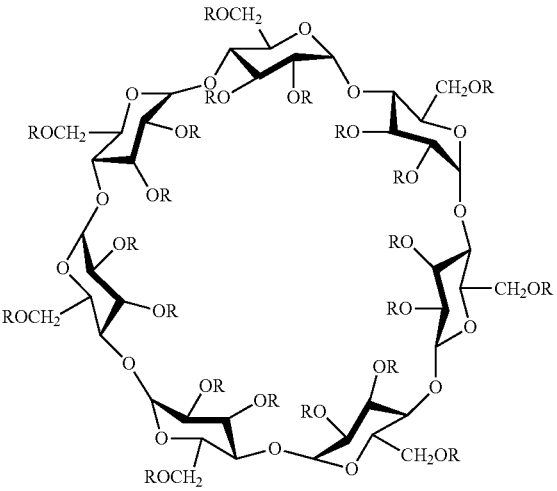

(III)

wherein each R is independently selected from H or —$(CH_2)_4$—$SO_3Na$, wherein the composition comprises a plurality of different compounds of Formula III, wherein the average number of substitutions for the substituent R is —$(CH_2)_4$—$SO_3Na$ for the plurality of different compounds is from 6.0 to 7.1, wherein the sole active ingredient in the composition is topiramate or a salt thereof.

4. A method for treating a subject who has or is at risk for developing a condition selected from the group consisting of epilepsy, seizures, anoxia, stroke, status epilepticus, refractory status epilepticus, gambling addiction, migraines, substance dependence, alcoholism, cocaine dependence, nicotine dependence, metabolic syndrome X, diabetes mellitus type 2, vomiting, obsessive-compulsive disorder, refractory generalized social phobia, Tourette syndrome, levodopa-induced dyskinesia in Parkinson's Disease, refractory POS, Prader-Willi syndrome, multiple sclerosis, Lennox-Gastaut syndrome, Dravet's syndrome, bipolar disorder, obesity, post-traumatic stress disorder, cluster headaches, severe headaches, conditions caused by exposure to a chemical warfare nerve agent, hypoxic-ischemic encephalopathy, subdural hematoma, periventricular leukomalacia, mental retardation, grey matter injury, white matter injury, and an infection, the method consisting essentially of administering to a subject in need thereof an effective amount of a composition comprising topiramate or a salt thereof, and a compound of Formula I:

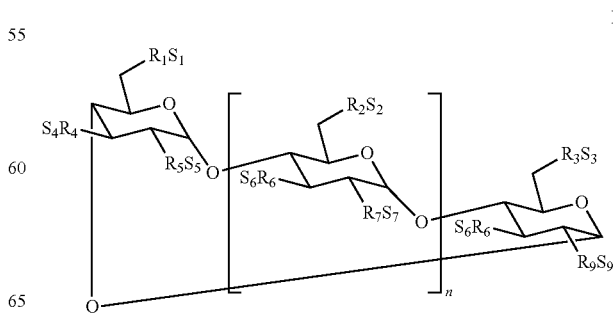

I wherein: n is 4, 5 or 6; $R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$ and $S_9$ are each, independently, H or a pharmaceutically acceptable cation, wherein the sole active ingredient in the composition is topiramate or a salt thereof.

5. The method of claim 4, wherein at least one of $R_1$ and $R_2$ is independently a —O—($C_2$-$C_6$ alkylene)$SO_3^-$ group that is a —O—$(CH_2)_m SO_3^-$ group, wherein m is 2 to 6, and the pharmaceutically acceptable cation is H, an alkali metal, an alkaline earth metal, an ammonium ion, or an amine cation.

6. The method of claim 4, wherein the compound of Formula I is a compound of Formula III:

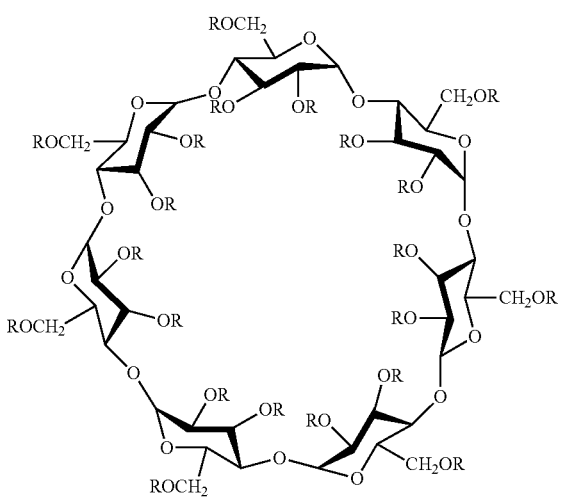

III wherein each R is independently selected from H or —$(CH_2)_4$—$SO_3Na$, wherein the composition comprises a plurality of different compounds of Formula III, wherein the average number of substitutions for the substituent R is —$(CH_2)_4$—$SO_3Na$ for the plurality of different compounds is from 6.0 to 7.1.

7. The method of claim 4, wherein the method consists of administering the composition to the subject.

8. The method of claim 4, wherein the composition consists essentially of topiramate, or a salt thereof, the compound of Formula I and a pharmaceutically acceptable carrier.

9. The method of claim 4, wherein the composition consists of topiramate, or a salt thereof, the compound of Formula I and a pharmaceutically acceptable carrier.

10. The method of claim 4, wherein the effective amount comprises about 0.2 mg/kg/day to about 50 mg/kg/day topiramate.

11. The method of claim 4, wherein the compound of Formula I and topiramate are present in a ratio greater than or equal to about 1.4:1.

12. The method of claim 4, wherein the compound of Formula I and topiramate are present in a ratio of about 1.4:1 to about 5:1.

13. The method of claim 4, wherein the compound of Formula I and topiramate are present in a ratio of about 1.4:1.

14. The method of claim 4, wherein the composition is administered daily.

15. The method of claim 4, wherein the administration is parenteral.

16. The method of claim 4, wherein the administration is intravenous.

17. The method of claim 4, wherein the administration is intramuscular.

18. The method of claim 4, wherein the subject is a neonate.

19. The method of claim 18, wherein the condition is selected from the group consisting of hypoxic-ischemic encephalopathy, subdural hematoma, periventricular leukomalacia, mental retardation, grey matter injury, white matter injury, and an infection.

20. The method of claim 4, wherein the condition is selected from the group consisting of epilepsy, seizures, status epilepticus, refractory status epilepticus, migraines, Lennox-Gastaut syndrome, cluster headaches, and severe headaches.

* * * * *